US012557993B2

(12) United States Patent
Mulliken et al.

(10) Patent No.:  US 12,557,993 B2
(45) Date of Patent:       Feb. 24, 2026

(54) TEMPERATURE DETECTION

(71) Applicant: Apple Inc., Cupertino, CA (US)

(72) Inventors: Grant H Mulliken, Sunnyvale, CA
(US); Cameron A Harder, Sunnyvale,
CA (US); Fletcher R Rothkopf, Los
Altos, CA (US); Izzet B Yildiz,
Sunnyvale, CA (US); **Nicholas C
Soldner**, Sunnyvale, CA (US)

(73) Assignee: Apple Inc., Cupertino, CA (US)

( * ) Notice: Subject to any disclaimer, the term of this
patent is extended or adjusted under 35
U.S.C. 154(b) by 123 days.

(21) Appl. No.: 18/568,258

(22) PCT Filed: Jun. 8, 2022

(86) PCT No.: PCT/US2022/032687
§ 371 (c)(1),
(2) Date: Dec. 7, 2023

(87) PCT Pub. No.: WO2022/261217
PCT Pub. Date: Dec. 15, 2022

(65) Prior Publication Data
US 2024/0268682 A1      Aug. 15, 2024

Related U.S. Application Data

(60) Provisional application No. 63/209,905, filed on Jun.
11, 2021.

(51) Int. Cl.
*A61B 5/01*          (2006.01)
*A61B 5/00*          (2006.01)
(52) U.S. Cl.
CPC .............. *A61B 5/01* (2013.01); *A61B 5/6803*
(2013.01); *A61B 5/742* (2013.01); *A61B*
*2560/0223* (2013.01); *A61B 2562/0271*
(2013.01)

(58) Field of Classification Search
CPC ......... A61B 5/01; A61B 5/6803; A61B 5/742;
A61B 2562/0271; G06F 3/013
See application file for complete search history.

(56) References Cited

U.S. PATENT DOCUMENTS

2010/0295769 A1* 11/2010 Lundstrom ............. G06F 3/011
345/156
2013/0021373 A1     1/2013 Vaught et al.
(Continued)

FOREIGN PATENT DOCUMENTS

GB          2286684 A  *  8/1995  ............ G01K 13/20
GB          2569323       6/2019

OTHER PUBLICATIONS

Johnson et al., "Thermographic Eye Temperature as an Index to
Body Temperature in Ponies" Journal of Equine Veterinary Science
31 (2011) 63-66 (Year: 2011).*

*Primary Examiner* — Boniface N Nganga
(74) *Attorney, Agent, or Firm* — Robert C. Kowert;
Kowert, Hood, Munyon, Rankin & Goetzel, P.C.

(57)                ABSTRACT

Methods and apparatus for measuring biometric data includ-
ing temperature in head-mounted devices (HMDs). Thermal
sensors may also be integrated into the HMD and used to
collect thermal data from the surface of the user's face. This
thermal data may, for example, be processed to determine
core body temperature of the user, or be processed to
generate estimates of the user's respiration. The temperature
data and/or respiration rate and changes to respiration rate
derived from signals from the sensors may be used to
generate and present biometric data to the user.

19 Claims, 11 Drawing Sheets

100

102

110

192              104

100

102

110

192         104

(56)        References Cited

U.S. PATENT DOCUMENTS

| | | | |
|---|---|---|---|
| 2016/0180078 A1* | 6/2016 | Chhabra | ................ G06F 21/57 |
| | | | 726/19 |
| 2018/0096533 A1* | 4/2018 | Osman | ................... G06T 17/10 |
| 2020/0085311 A1 | 3/2020 | Tzvieli et al. | |
| 2020/0174262 A1* | 6/2020 | Godar | .................... G06F 3/015 |

* cited by examiner

100

100

TEMPERATURE DETECTION

PRIORITY APPLICATION

This application is a 371 of PCT Application No. PCT/ US2022/032687, Filed Jun. 8, 2022, which claims benefit of priority to U.S. Provisional Patent Application No. 63/209, 905, filed Jun. 11, 2021. The above applications are incorporated herein by reference. To the extent that any material in the incorporated application conflicts with material expressly set forth herein, the material expressly set forth herein controls.

BACKGROUND

Virtual reality (VR) allows users to experience and/or interact with an immersive artificial environment, such that the user feels as if they were physically in that environment. For example, virtual reality systems may display stereoscopic scenes to users in order to create an illusion of depth, and a computer may adjust the scene content in real-time to provide the illusion of the user moving within the scene. When the user views images through a virtual reality system, the user may thus feel as if they are moving within the scenes from a first-person point of view. Similarly, mixed reality (MR) combines computer generated information (referred to as virtual content) with real world images or a real world view to augment, or add content to, a user's view of the world. The simulated environments of VR and/or the mixed environments of MR may thus be utilized to provide an interactive user experience for multiple applications, such as applications that add virtual content to a real-time view of the viewer's environment, interacting with virtual training environments, gaming, remotely controlling drones or other mechanical systems, viewing digital media content, interacting with the Internet, or the like.

Respiration detection has been conventionally performed using a wearable band worn by a subject and/or using a flow-meter in line with a user's mouth or nose (or both). However, these conventional methods are not designed for long-term user comfort, and cannot easily be integrated in head-mounted devices (HMDs), such as HMDs used in VR/MR systems.

Audio accelerometers have been used for contact-based extraction of speech through the physics of bone-conduction between the voice box and head. The most widespread use of bone-conduction accelerometers are found in wireless headphones. These conventional audio accelerometers are extremely sensitive and support broadband frequencies up to 4 kHz.

Some conventional systems have employed contact-based sensors such as thermistors and thermocouples, which can be challenging to integrate in small form factor devices and require low thermal mass designs that require constant contact with the skin.

Some conventional systems use expensive thermal imaging cameras with resolutions of 320×240 or more, and apply standard image processing approaches to extract facial features and isolate regions of known large thermal delta (nose, mouth). However these approaches require an outward view of the user, and the cameras tend to be relatively large and expensive.

SUMMARY

Embodiments of methods and apparatus for temperature detection are described. The methods and apparatus may, for example, be implemented in a head-mounted device (HMD), such as a headset, helmet, goggles, or glasses. Embodiments of thermal sensors that may be integrated in an HMD for estimating body temperature (e.g., core body temperature) are described. Embodiments may allow body temperature of a user to be measured with integrated thermal sensors while wearing an HMD. The thermal sensors that may be used to measure body temperature in an HMD may include contact sensors, non-contact sensors, or both.

Contact sensors may, for example be mounted on or integrated in a nose pad, a light seal, in a nasal mount, or elsewhere in the HMD. Thermal contact sensors may include thermistor and/or thermocouple technology sensors.

Non-contact sensors may, for example be mounted on or integrated in a nose pad, a light seal, a nasal mount, or elsewhere in the HMD. Thermal non-contact sensors may include, but are not limited to, passive IR sensors that include one or more pixels. Passive IR sensors may be used to measure temperature at the surface of the nose, or in other places such as the forehead, temple, or in the region around the eye.

In some embodiments, instead of or in addition to contact sensors and passive IR sensors, visible light (RGB) cameras of the HMD may be used to measure changes in luminance levels; this information may be analyzed to derive changes in body temperature. Similarly, in some embodiments, instead of or in addition to passive IR sensors, information captured with IR cameras of the HMD, for example IR cameras that are used in gaze tracking, may be subsampled and analyzed to derive changes in body temperature.

Information derived from signals collected from the thermal sensors in an HMD may be used in a variety of applications. For example, detected fluctuations in temperature may be used to derive changes in respiration.

Temperature data collected by the thermal sensors of an HMD, and/or respiration data derived from the thermal data, may be recorded or stored to memory of the HMD or on a device external to the HMD. The recorded data may, for example, be used to track biometric data for the user over time.

Figure 1A:
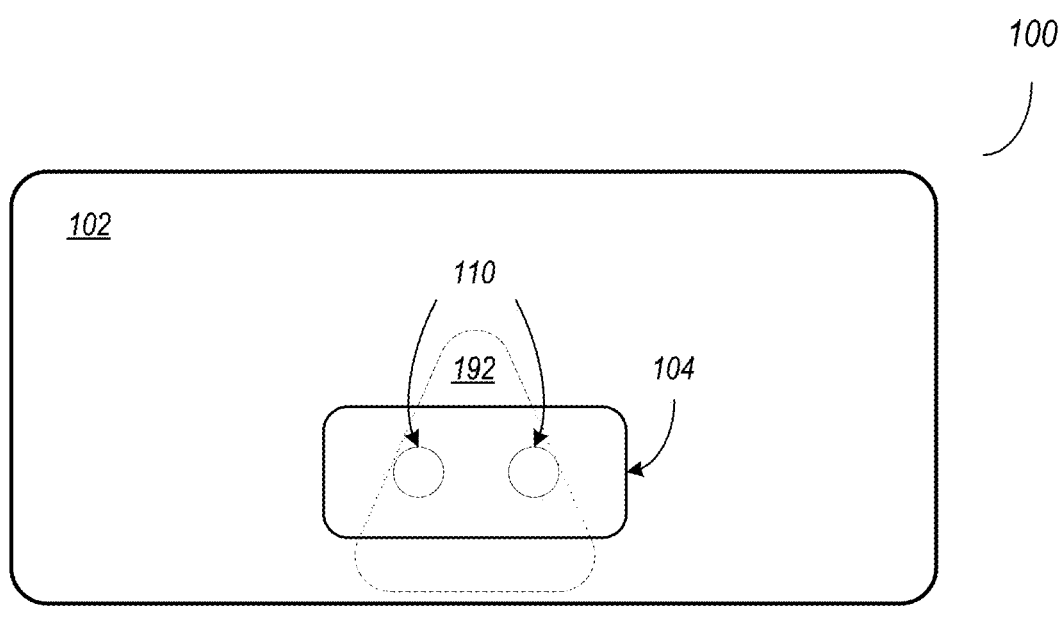
FIGS. 1A and 1B illustrate biometric sensors on a nasal mounting component of an example head-mounted device (HMD), according to some embodiments.

This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

"Comprising." This term is open-ended. As used in the claims, this term does not foreclose additional structure or steps. Consider a claim that recites: "An apparatus comprising one or more processor units . . . ." Such a claim does not foreclose the apparatus from including additional components (e.g., a network interface unit, graphics circuitry, etc.).

"Configured To." Various units, circuits, or other components may be described or claimed as "configured to" perform a task or tasks. In such contexts, "configured to" is used to connote structure by indicating that the units/circuits/components include structure (e.g., circuitry) that performs those task or tasks during operation. As such, the unit/circuit/component can be said to be configured to perform the task even when the specified unit/circuit/component is not currently operational (e.g., is not on). The units/circuits/components used with the "configured to" language include hardware—for example, circuits, memory storing program instructions executable to implement the operation, etc. Reciting that a unit/circuit/component is "configured to" perform one or more tasks is expressly intended not to invoke 35 U.S.C. § 112, paragraph (f), for that unit/circuit/component. Additionally, "configured to" can include generic structure (e.g., generic circuitry) that is manipulated by software or firmware (e.g., an FPGA or a general-purpose processor executing software) to operate in manner that is capable of performing the task(s) at issue. "Configure to" may also include adapting a manufacturing process (e.g., a semiconductor fabrication facility) to fabricate devices (e.g., integrated circuits) that are adapted to implement or perform one or more tasks.

"First," "Second," etc. As used herein, these terms are used as labels for nouns that they precede, and do not imply any type of ordering (e.g., spatial, temporal, logical, etc.). For example, a buffer circuit may be described herein as performing write operations for "first" and "second" values. The terms "first" and "second" do not necessarily imply that the first value must be written before the second value.

"Based On" or "Dependent On." As used herein, these terms are used to describe one or more factors that affect a determination. These terms do not foreclose additional factors that may affect a determination. That is, a determination may be solely based on those factors or based, at least in part, on those factors. Consider the phrase "determine A based on B." While in this case, B is a factor that affects the determination of A, such a phrase does not foreclose the determination of A from also being based on C. In other instances, A may be determined based solely on B.

"Or." When used in the claims, the term "or" is used as an inclusive or and not as an exclusive or. For example, the phrase "at least one of x, y, or z" means any one of x, y, and z, as well as any combination thereof.

DETAILED DESCRIPTION

Various embodiments of methods and apparatus for measuring biometric data including respiration and temperature in head-mounted devices (HMDs) are described. Embodiments of methods and apparatus for detecting respiration of users of HMDs are described. In addition, embodiments of method and apparatus for detecting temperature (e.g., core body temperature) of users of HMDs are described. These methods and apparatus may be used alone or in combination. In some embodiments, thermal data may be collected using contact or non-contact sensors and analyzed to determine respiration rate or changes. In some embodiments, motion data may be collected using contact sensors (high-bandwidth accelerometers) and analyzed, alone or in combination with thermal data, to determine respiration rate or changes.

In some embodiments, accelerometers and/or thermal sensors (e.g., passive infrared (IR) sensors) may be located at or near the surface of a user's nose, for example integrated in a nasal mounting component (referred to as a nasal mount), and data from those sensors may be used to determine respiration rate or change. Embodiments of contact-based, high bandwidth audio accelerometers, also referred to as motion sensors, are described that are roughly 2×2 mm in size that may, for example, be fitted in a nose piece so as to contact the surface of a user's nose; motion data from the surface collected by these sensors may be analyzed and used to estimate respiration rate and/or detect changes in respiration. In some embodiments, thermal sensors may be implemented as single-pixel or small multi-pixel (e.g., 4×4) non-contact passive infrared detectors. These thermal sensors may be fitted in a nose piece so as to view the surface of a user's nose; thermal data from the surface collected by these sensors may be analyzed and used to estimate respiration rate and/or detect changes in respiration. In some embodiments, thermal sensors and/or accelerometers may be located elsewhere on the HMD, for example on the forehead, or at or near the user's ears. In some embodiments, the HMD may include a light seal that may fit relatively snugly on the face around the user's eyes, and one or more motion sensors and/or thermal sensors may be integrated in the light seal.

In some embodiments, signals from cameras integrated in an HMD, for example IR cameras used in gaze tracking or visible light cameras used for capturing images of portions of the user's face, may be subsampled in regions of interest, and the subsampled data may be analyzed to estimate surface temperature or changes in temperature. This analyzed data may, for example, be used in determining respiration or changes in respiration, alone or in combination with data collected from other sensors.

In some embodiments, other biometric sensors, such as photo-plethysmography (PPG) sensors, may be integrated in an HMD; data collected from these other sensors may be used alone or in combination with the respiration and temperature data collected by the motion and thermal sensors of the HMD, for example to report current biometric data to the user as feedback, recorded for use in tracking biometric data over time, and so on.

In some embodiments, biometric data, including one or more of, but not limited to, thermal data, pulse, and respiration data, may be collected by sensors on devices external to the HMD, for example from a wristband, headphones, or earbuds. Data collected from these sensors in other devices may be used alone or in combination with the data collected by the sensors of the HMD, for example to report current biometric data to the user as feedback, recorded for use in tracking biometric data over time, and so on.

The methods and apparatus described herein may, for example, be implemented in a head-mounted device (HMD), such as a headset, helmet, goggles, or glasses. Embodiments of example HMDs are further described with respect to FIGS. 9 and 10.

Figure 1B:
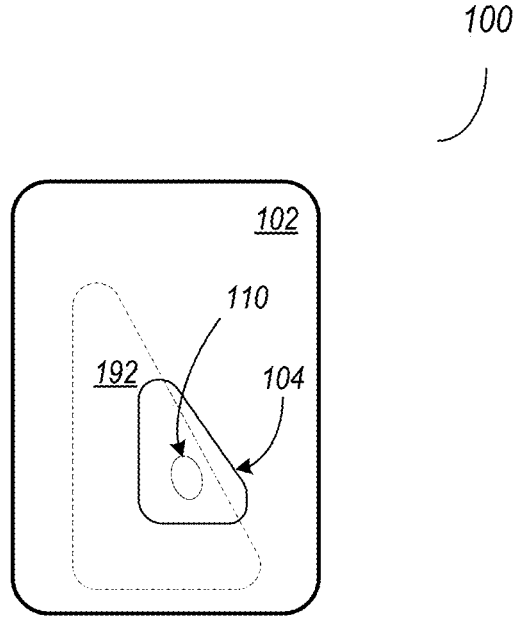

FIGS. 1A and 1B illustrate biometric sensors on a nasal mounting component, or nasal mount, of an example head-mounted device (HMD) 100, according to some embodiments. FIG. 1A shows a front view of the HMD 100, and FIG. 1B shows a side view of the HMD 100. The HMD 100 includes a frame 102 (e.g., a headset, helmet, goggles, or glasses frame). In embodiments that include a glasses frame, the frame may be a foldable frame with sensors located in the frame portion that holds the lenses and/or on the foldable arms. A nasal mount 104 may be coupled to or integrated in the frame 102. For example, nasal mount 104 may be a flexible strip configured to fit relatively snugly across the bridge of a user's nose 192 when the user is wearing the HMD 100. As another example, nasal mount 104 may be a nosepiece of the frame 102. One or more biometric sensors 110 may be integrated in the nasal mount 104. The sensors 110 may include one or more motion sensors (e.g., accelerometers including but not limited to audio accelerometers) and/or one or more thermal sensors (e.g., thermistors, thermocouples, thermal imaging sensors, etc.). The sensors 110 may include contact sensors (sensors that contact the surface of the nose 192), non-contact sensors (sensors that do not contact the surface of the nose 192), or both.

In some embodiments, a contact sensor 110 may be integrated in a diaphragm component of the nasal mount 104; the diaphragm may be configured to provide a spring action to ensure contact of the sensor 110 with the surface of the nose 192. In some embodiments, a non-contact sensor 110 may be integrated in a diaphragm component of the nasal mount 104; the diaphragm may be configured provide movement of the sensor on multiple axes to ensure that the sensor 110 is aligned at least approximately normal to the surface of the nose 192 while not contacting the surface, and/or to ensure a proper distance from the surface of the nose 192 is maintained.

In some embodiments, sensors 110 may include one or more contact-based high bandwidth audio accelerometers, also referred to as motion sensors, that are roughly 2×2 mm in size and that may contact the surface of a user's nose. Motion data from the user's face collected by these motion sensors 110 may be analyzed and used to estimate respiration rate and/or detect changes in respiration. Note that the motion sensors may sense motion at the surface and/or beneath the surface of the face, and sensed motion may include motion of the skin, muscles, bones, and/or head.

In some embodiments, sensors 110 may include one or more thermal sensors implemented as single-pixel or small multi-pixel (e.g., 4×4) non-contact infrared detectors. These thermal sensors 110 may face the surface of a user's nose 192 to collect thermal data from the surface. Thermal data collected from the surface by the thermal sensors 110 may be analyzed and used to estimate respiration rate and/or detect changes in respiration, alone or in combination with motion data collected by one or more motion sensors 110. In some embodiments, thermal data collected by the thermal sensors 110 may instead or also be used to estimate core body temperature.

FIGS. 5A-5B and 6A-6B illustrate example contact and non-contact biometric sensors 110 that may, for example, be integrated in a nasal mount 104 in various embodiments.

While not shown in FIGS. 1A and 1B, in some embodiments, in addition to sensors 110 of nose mount 104, thermal sensors and/or motion sensors may be located elsewhere on the HMD 100, for example at the forehead, or at or near the user's ears. In some embodiments, the HMD 100 may include a light seal that may fit relatively snugly on the face around the user's eyes, and one or more motion sensors and/or thermal sensors may be integrated in the light seal.

In some embodiments, other biometric sensors, such as photo-plethysmography (PPG) sensors, may be integrated in an HMD 100; data collected from these other sensors may be used alone or in combination with the respiration and temperature data collected by the motion and thermal sensors 110 of the HMD 100, for example to report current biometric data to the user as feedback, recorded for use in tracking biometric data over time, and so on.

In some embodiments, biometric data, including one or more of, but not limited to, thermal data, pulse, and respiration data, may be collected by sensors on devices external to the HMD 100, for example from a wristband, headphones, or earbuds. Data collected from these sensors in other devices may be used alone or in combination with the data collected by the sensors of the HMD 100, for example to report current biometric data to the user as feedback, to be recorded for use in tracking biometric data over time, and so on.

Figure 2A:
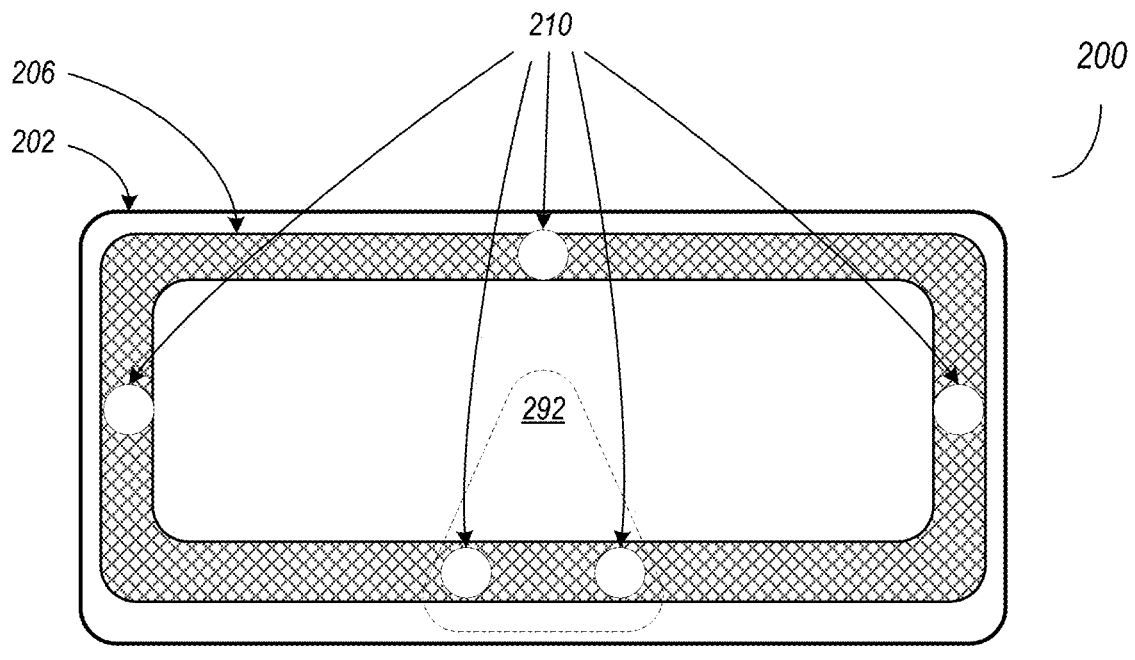
FIGS. 2A and 2B illustrate biometric sensors integrated in a light seal of an example HMD, according to some embodiments.
Figure 2B:
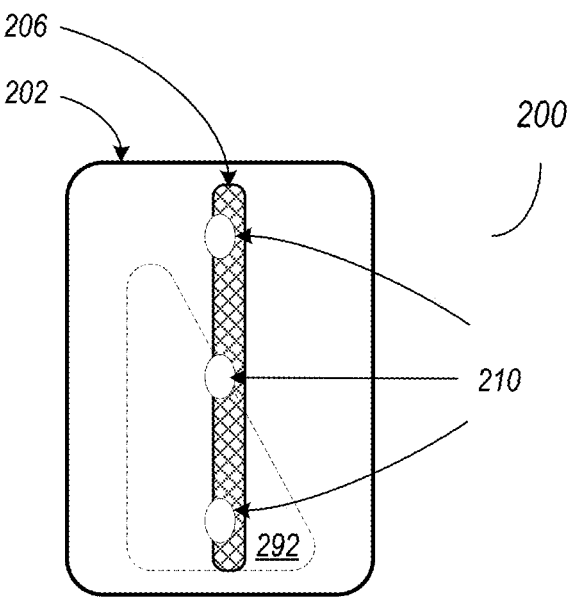

FIGS. 2A and 2B illustrate biometric sensors integrated in a light seal of an HMD 200, according to some embodiments. FIG. 2A shows a front view of the HMD 200, and FIG. 2B shows a side view of the HMD 200. The HMD 200 includes a frame 202 (e.g., a headset, helmet, goggles, or glasses frame). In some embodiments, the HMD 200 may include a light seal 206 that may fit relatively snugly on the face around the user's eyes and nose. One or more sensors 210, including but not limited to motion sensors and/or thermal sensors, may be integrated in the light seal 206 at one or more locations. This example shows sensors 210 located on the forehead, at or near the temples, and on the bridge of the nose 292 where the light seal 206 contacts the user's face. However, sensors 210 may be located elsewhere on the light seal 206.

The sensors 210 may include one or more motion sensors (e.g., accelerometers including but not limited to audio accelerometers) and/or one or more thermal sensors (e.g., thermistors, thermocouples, thermal imaging sensors, etc.). The sensors 210 may include contact sensors (sensors that contact the surface of the face under the light seal 206), non-contact sensors (sensors that do not contact the surface of the face under the light seal 206), or both.

In some embodiments, a contact sensor 210 may be integrated in a diaphragm component; the diaphragm may be configured to provide a spring action to ensure contact of the sensor 210 with the surface of the face. In some embodiments, a non-contact sensor 210 may be integrated in a diaphragm component; the diaphragm may be configured provide movement of the sensor on multiple axes to ensure that the sensor 210 is aligned at least approximately normal to the surface of the face while not contacting the surface, and/or to ensure a proper distance from the surface is maintained.

In some embodiments, sensors 210 may include one or more contact-based audio accelerometers, also referred to as motion sensors, that are roughly 2×2 mm in size and that may contact the surface of the face. Motion data from the user's face collected by these motion sensors 210 may be analyzed and used to estimate respiration rate and/or detect changes in respiration.

In some embodiments, sensors 210 may include one or more thermal sensors implemented as single-pixel or small multi-pixel (e.g., 4×4) non-contact infrared detectors. These thermal sensors 210 may face the surface of the user's face (or other regions of the user's head) to collect thermal data from the surface. Thermal data collected from the surface by the thermal sensors 210 may be analyzed and used to estimate respiration rate and/or detect changes in respiration, alone or in combination with motion data collected by one or more motion sensors 210. In some embodiments, thermal data collected by the thermal sensors 210 may instead or also be used to estimate core body temperature.

FIGS. 5A-5B and 6A-6B illustrate example contact and non-contact biometric sensors 210 that may, for example, be integrated in a light seal 206 in various embodiments.

While not shown in FIGS. 2A and 2B, in some embodiments, in addition to sensors 210 integrated in light seal 206, thermal sensors and/or motion sensors may be located elsewhere on the HMD 200, for example or at or near the user's ears.

In some embodiments, other biometric sensors, such as photo-plethysmography (PPG) sensors, may be integrated in an HMD 200; data collected from these other sensors may be used alone or in combination with the respiration and temperature data collected by the motion and thermal sensors in the light seal 206 of the HMD 200, for example to report current biometric data to the user as feedback, recorded for use in tracking biometric data over time, and so on.

In some embodiments, biometric data, including one or more of, but not limited to, thermal data, pulse, and respiration data, may be collected by sensors on devices external to the HMD 200, for example from a wristband, headphones, or earbuds. Data collected from these sensors in other devices may be used alone or in combination with the data collected by the sensors of the HMD 200, for example to report current biometric data to the user as feedback, recorded for use in tracking biometric data over time, and so on.

Figure 3A:
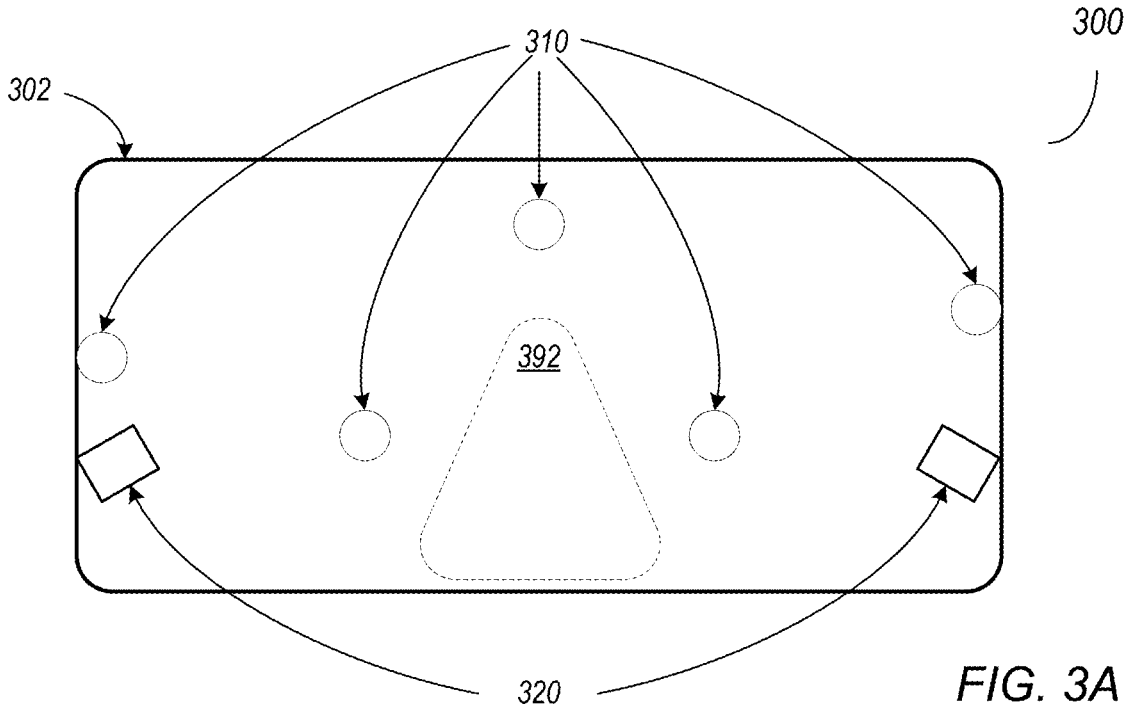
FIGS. 3A and 3B illustrate sensors and cameras that may be used to collect biometric data in an example HMD, according to some embodiments.
Figure 3B:
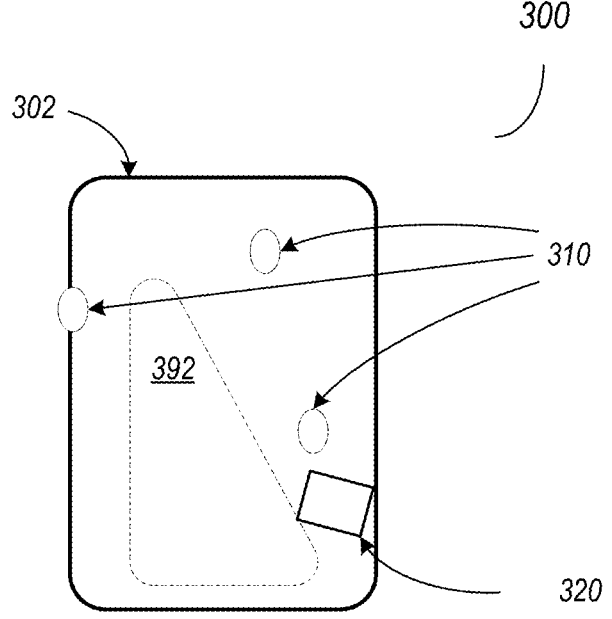

FIGS. 3A and 3B illustrate sensors and cameras that may be used to collect biometric data in an HMD, according to some embodiments. FIG. 3A shows a front view of the HMD 300, and FIG. 3B shows a side view of the HMD 300. The HMD 300 includes a frame 302 (e.g., a headset, helmet, goggles, or glasses frame). In some embodiments, the HMD 300 may include a light seal (not shown) that may fit relatively snugly on the face around the user's eyes and nose 392, for example as shown in FIGS. 2A-2B. One or more sensors 310, including but not limited to motion sensors and/or thermal sensors, may be integrated in or attached to the HMD 300 at one or more locations. This example shows sensors 310 located on the forehead, at or near the temples, and on or near the nose 392. However, sensors 310 may be located elsewhere on the HMD 300.

The sensors 310 may include one or more motion sensors (e.g., accelerometers including but not limited to audio accelerometers) and/or one or more thermal sensors (e.g., thermistors, thermocouples, thermal imaging sensors, etc.). The sensors 310 may include contact sensors (sensors that contact the surface of the face, non-contact sensors (sensors that do not contact the surface of the face), or both.

In some embodiments, a contact sensor 310 may be integrated in a diaphragm component; the diaphragm may be configured to provide a spring action to ensure contact of the sensor 310 with the surface of the face. In some embodiments, a non-contact sensor 310 may be integrated in a diaphragm component; the diaphragm may be configured provide movement of the sensor on multiple axes to ensure that the sensor 310 is aligned at least approximately normal to the surface of the face while not contacting the surface, and/or to ensure a proper distance from the surface is maintained.

In some embodiments, sensors 310 may include one or more contact-based audio accelerometers, also referred to as motion sensors, that are roughly 2×2 mm in size and that may contact the surface of the face. Motion data from the user's face collected by these motion sensors 310 may be analyzed and used to estimate respiration rate and/or detect changes in respiration.

In some embodiments, sensors 310 may include one or more thermal sensors implemented as single-pixel or small multi-pixel (e.g., 4×4) non-contact infrared detectors. These thermal sensors 310 may face the surface of the user's face to collect thermal data from the surface. Thermal data collected from the surface by the thermal sensors 310 may be analyzed and used to estimate respiration rate and/or detect changes in respiration, alone or in combination with motion data collected by one or more motion sensors 310. In some embodiments, thermal data collected by the thermal sensors 310 may instead or also be used to estimate core body temperature.

FIGS. 5A-5B and 6A-6B illustrate example contact and non-contact biometric sensors 210 that may, for example, be integrated in a light seal 206 in various embodiments.

In some embodiments, other components of an HMD 300 may be used in determining temperature and/or respiration. In some embodiments, for example, visible light and/or IR cameras 320 that are used for other purposes may be leveraged to collect biometric data. As an example, signals from IR cameras 320 used in gaze tracking and/or from visible light cameras 320 used for capturing images of portions of the user's face may be subsampled in regions of interest, and the subsampled data may be analyzed to estimate surface temperature or changes in temperature. This analyzed data may, for example, be used in determining respiration or changes in respiration, alone or in combination with data collected from other sensors 310.

In some embodiments, other biometric sensors, such as photo-plethysmography (PPG) sensors, may be integrated in an HMD 300; data collected from these other sensors may be used alone or in combination with the respiration and temperature data collected by the motion and thermal sensors 310 of the HMD 300, for example to report current biometric data to the user as feedback, recorded for use in tracking biometric data over time, and so on.

In some embodiments, biometric data, including one or more of, but not limited to, thermal data, pulse, and respiration data, may be collected by sensors on devices external to the HMD 300, for example from a wristband, headphones, or earbuds. Data collected from these sensors in other devices may be used alone or in combination with the data collected by the sensors of the HMD 300, for example to report current biometric data to the user as feedback, recorded for use in tracking biometric data over time, and so on.

Figure 4A:
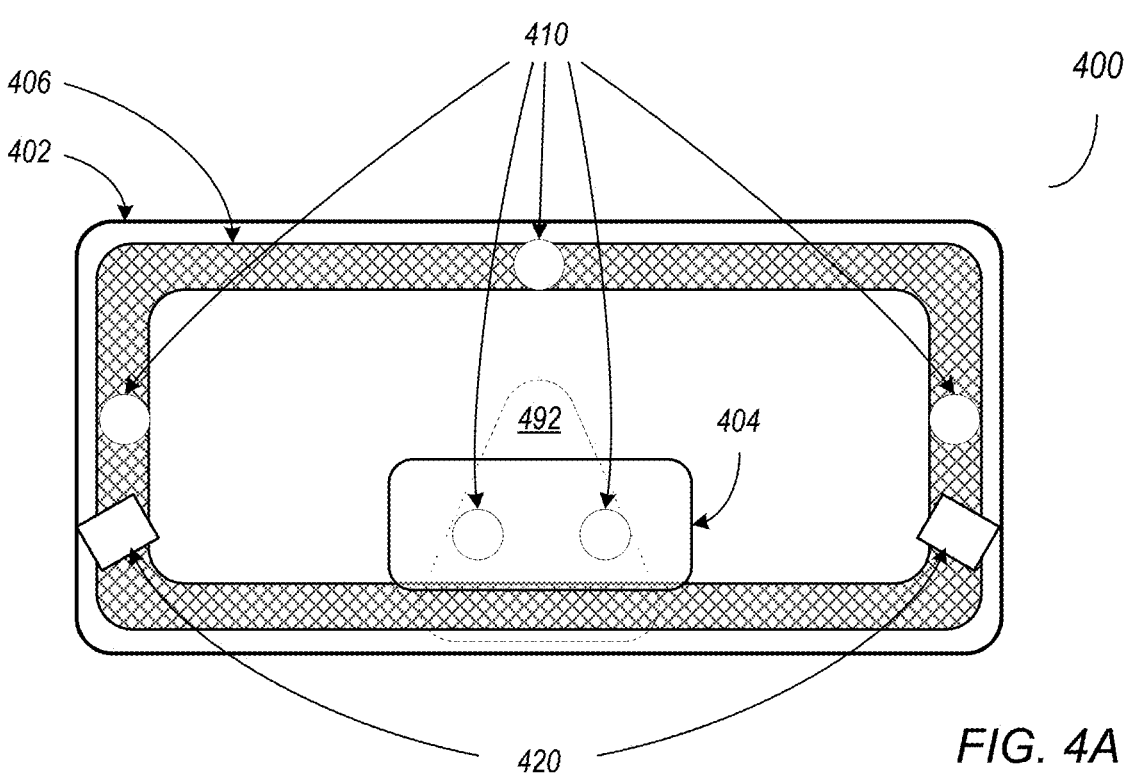
FIGS. 4A and 4B illustrate multiple sensors and cameras located on different components of an example HMD, according to some embodiments.
Figure 4B:
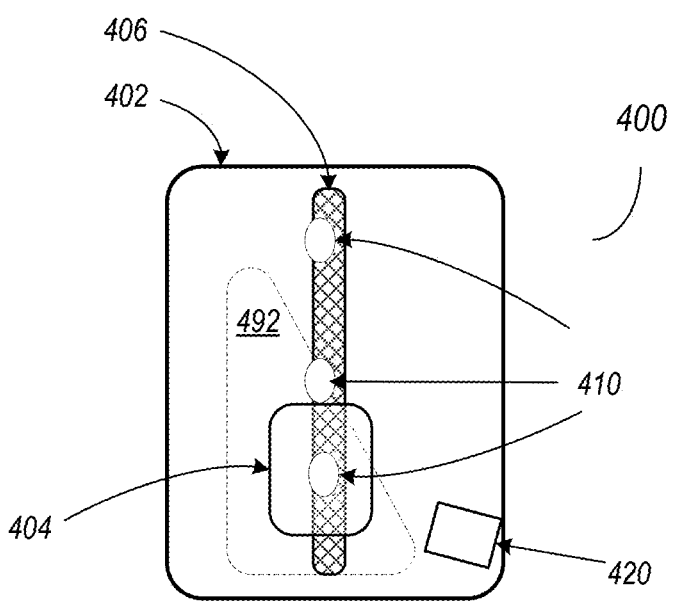

FIGS. 4A and 4B illustrate multiple sensors and cameras located on different components of an HMD, according to some embodiments. FIG. 4A shows a front view of the HMD 400, and FIG. 4B shows a side view of the HMD 400. The HMD 400 includes a frame 402 (e.g., a headset, helmet, goggles, or glasses frame). A nasal mount 404 may be coupled to or integrated in the frame 402. For example, nasal mount 404 may be a flexible strip configured to fit relatively snugly across the bridge of a user's nose 492 when the user is wearing the HMD 400. As another example, nasal mount 404 may be a nosepiece of the frame 402. One or more biometric sensors 410 may be integrated in the nasal mount 404. The sensors 410 may include one or more motion sensors (e.g., accelerometers including but not limited to audio accelerometers) and/or one or more thermal sensors (e.g., thermistors, thermocouples, thermal imaging sensors, etc.). The sensors 410 may include contact sensors (sensors that contact the surface of the nose 492), non-contact sensors (sensors that do not contact the surface of the nose 492), or both.

In some embodiments, the HMD 200 may also include a light seal 406 that may fit relatively snugly on the face around the user's eyes and nose. One or more sensors 410, including but not limited to motion sensors and/or thermal sensors, may be integrated in the light seal 406 at one or more locations. This example shows sensors 410 located on the forehead and at or near the temples. However, sensors 410 may be located elsewhere on the light seal 406.

In some embodiments, a contact sensor 410 may be integrated in a diaphragm component; the diaphragm may be configured to provide a spring action to ensure contact of the sensor 410 with the surface of the user's face. In some embodiments, a non-contact sensor 410 may be integrated in a diaphragm component; the diaphragm may be configured provide movement of the sensor on multiple axes to ensure that the sensor 410 is aligned at least approximately normal to the surface of the user's face while not contacting the surface, and/or to ensure a proper distance from the surface of the face is maintained.

In some embodiments, sensors 410 may include one or more contact-based audio accelerometers, also referred to as motion sensors, that are roughly 2×2 mm in size and that may contact the surface of a user's face. Motion data from the user's face collected by these motion sensors 410 may be analyzed and used to estimate respiration rate and/or to detect changes in respiration.

In some embodiments, sensors 410 may include one or more thermal sensors implemented as single-pixel or small multi-pixel (e.g., 4×4) non-contact infrared detectors. These thermal sensors 410 may face the surface of a user's face (or other regions of the user's head) to collect thermal data from the surface. Thermal data collected from the surface by the thermal sensors 410 may be analyzed and used to estimate respiration rate and/or detect changes in respiration, alone or in combination with motion data collected by one or more motion sensors 410. In some embodiments, thermal data collected by the thermal sensors 410 may instead or also be used to estimate core body temperature.

While not shown in FIGS. 4A and 4B, in some embodiments, in addition to sensors 410 of nose mount 404 and light seal 406, thermal sensors and/or motion sensors may be located elsewhere on the HMD 400, for example at or near the user's ears.

FIGS. 5A-5B and 6A-6B illustrate example contact and non-contact biometric sensors 110 that may, for example, be integrated in a nasal mount 104 in various embodiments.

In some embodiments, other components of an HMD 400 may be used in determining temperature and/or respiration. In some embodiments, for example, visible light and/or IR cameras 420 that are used for other purposes may be leveraged to collect biometric data. As an example, signals from IR cameras 420 used in gaze tracking and/or from visible light cameras 420 used for capturing images of portions of the user's face may be subsampled in regions of interest, and the subsampled data may be analyzed to estimate surface temperature or changes in temperature. This analyzed data may, for example, be used in determining respiration or changes in respiration, alone or in combination with data collected from other sensors 410.

In some embodiments, other biometric sensors, such as photo-plethysmography (PPG) sensors, may be integrated in an HMD 400; data collected from these other sensors may be used alone or in combination with the respiration and temperature data collected by the motion and thermal sensors 410 of the HMD 400, for example to report current biometric data to the user as feedback, recorded for use in tracking biometric data over time, and so on.

In some embodiments, biometric data, including one or more of, but not limited to, thermal data, pulse, and respiration data, may be collected by sensors on devices external to the HMD 400, for example from a wristband, headphones, or earbuds. Data collected from these sensors in other devices may be used alone or in combination with the data collected by the sensors of the HMD 400, for example to report current biometric data to the user as feedback, recorded for use in tracking biometric data over time, and so on.

Figure 5A:
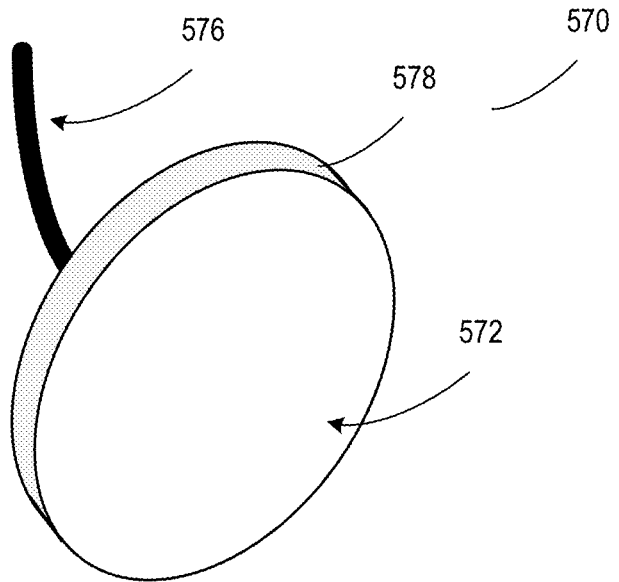
FIG. 5A illustrates an example contact sensor, according to some embodiments.

FIG. 5A illustrates an example contact sensor, according to some embodiments. Contact sensor 570 may, for example, be a thermal sensor or a motion sensor. A contact sensor 570 may include a component 578 such as a disk that includes sensing components; one surface 572 of the disk 578 contacts the user's skin. A contact sensor 570 may also include a lead 576 that couples the sensor to other sensors and/or a controller of an HMD and through which power (if necessary) is provided to the sensor 570 and through which signals collected by the sensor 570 are sent to, for example, the controller.

Thermal contact sensors 570 may include, but are not limited to, thermistors and thermocouples. A thermistor is an electrical resistor whose resistance is greatly reduced by heating; thermistors can be used to measure temperature. A thermocouple is a thermoelectric device for measuring temperature consisting of two wires of different metals connected at two points, a voltage is developed between the two junctions in proportion to the temperature difference. A motion sensor may, for example, be a contact-based audio accelerometer of roughly 2×2 mm in size. The accelerometer may detect vibrations; the signal from an accelerometer may be processed to determine motion of, for example, the surface of the nose. This motion information may, for example, be interpreted to estimation respiration rate, whether the user is breathing in or out, and changes in respiration.

Figure 5B:
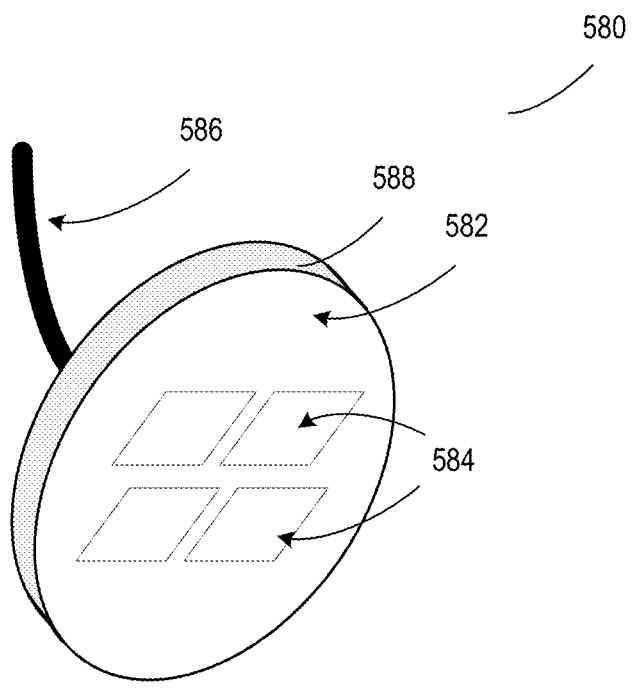
FIG. 5B illustrates an example non-contact sensor, according to some embodiments.

FIG. 5B illustrates an example non-contact sensor, according to some embodiments. Non-contact sensor 580 may, for example, be a thermal sensor or a motion sensor. A non-contact sensor 580 may include a component 588 such as a disk that includes sensing components; one surface 582 of the disk 588 faces, but does not contact, the user's skin. A non-contact sensor 580 may also include a lead 586 that couples the sensor to other sensors and/or a controller of an HMD and through which power (if necessary) is provided to the sensor 580 and through which signals collected by the sensor 580 are sent to, for example, the controller.

In some embodiments, a non-contact thermal sensor 580 may be a single-pixel or small multi-pixel (e.g., 4×4) infrared, non-contact thermal detector. This example shows a detector with four pixels 584; however, more or fewer pixels 584 may be used. A "hot" surface (e.g., a user's skin) emits infrared light, and the pixel(s) 584 detect that infrared light and send a signal to the controller. The signal may be analyzed to detect changes in the infrared emission, which can be interpreted to estimate changes in temperature at the surface of the skin. These changes may, for example, be mapped to changes in respiration, as the surface of the nose may cool when inhaling, and warm when exhaling. In some embodiments, thermal data collected by a thermal sensors 580 may instead or also be used to estimate core body temperature.

Figure 6A:
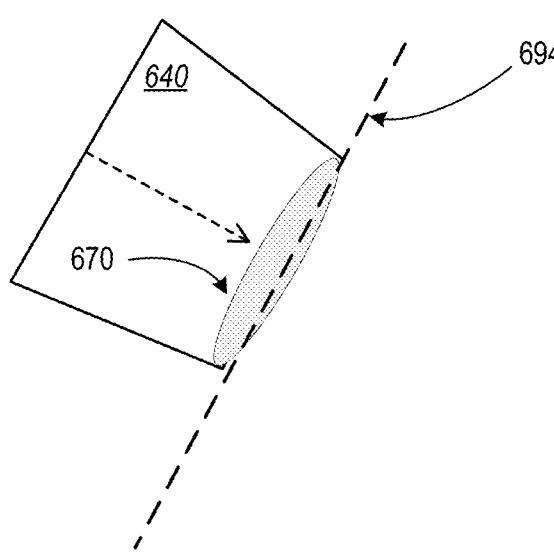
FIG. 6A illustrates an example contact sensor in a diaphragm, according to some embodiments.

FIG. 6A illustrates an example contact sensor in a diaphragm, according to some embodiments. In some embodiments, a contact sensor 670 may be integrated in a diaphragm 640; the diaphragm 640 may be configured to provide a spring action to ensure contact of the sensor 670 with the surface 694 of the user's face.

Figure 6B:
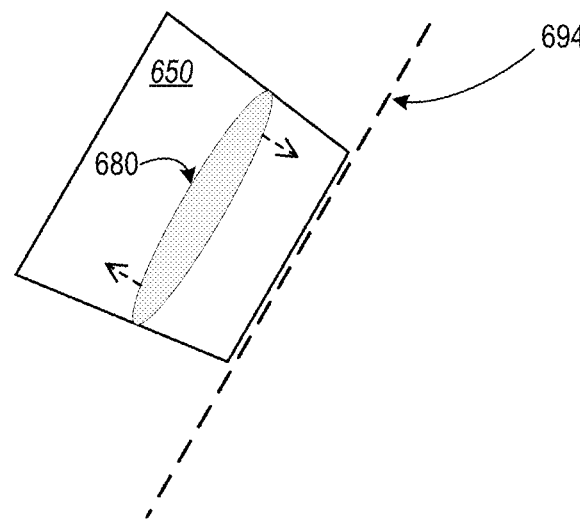
FIG. 6B illustrates an example non-contact sensor in a diaphragm, according to some embodiments.

FIG. 6B illustrates an example non-contact sensor in a diaphragm, according to some embodiments. In some embodiments, a non-contact sensor 680 may be integrated in a diaphragm 650; the diaphragm 650 may be configured provide movement of the sensor 680 on multiple axes to ensure that the sensor 680 is aligned with the surface 694 of the user's face while not contacting the surface 694, and/or to ensure a proper distance from the surface 694 is maintained.

Figure 7:
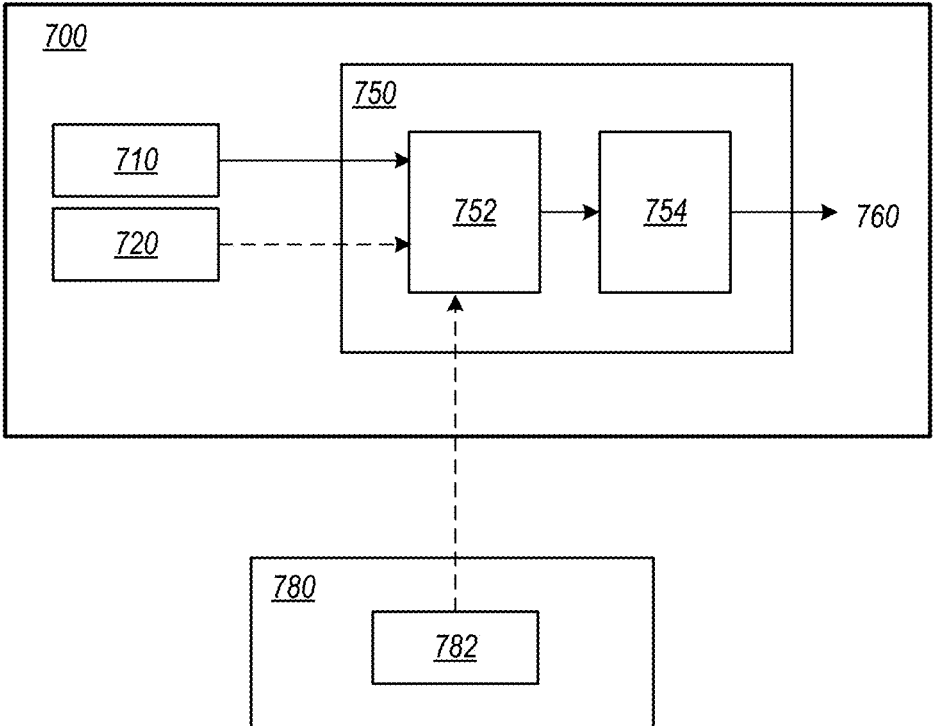
FIG. 7 is a block diagram illustrating processing of signals from sensors in an HMD, according to some embodiments.

FIG. 7 is a block diagram illustrating processing of signals from sensors in an HMD, according to some embodiments. An HMD 700 may include one or more contact and/or non-contact sensors 710. Sensors 710 may include motion sensors and/or thermal sensors as described herein, for example in reference to FIGS. 5A through 6B. The HMD 700 may also include one or more cameras 720 (e.g., infrared cameras). The sensors 710 and cameras 720 may couple to a controller 750 of the HMD that includes, but is not limited to, one or more processors and memory. The processors may include one or more processors 752 configured to pre-process signals from the sensors 710, and one or more processors 754 configured to analyze the pre-processed signals to estimate, generate, and output biometric information 760 including but not limited to temperature and respiration information.

Pre-processing signals from the sensors 710 by processors 752 may include applying any of various signal processing techniques to the signals. In some embodiments, pre-processing may include aligning the signals from two or more different sensors 710. This may be necessary because signals from different sensors, or from different types of sensors, may not be temporally aligned. For example, a signal from a motion sensor may show near-real-time correspondence with respiration, while a signal from a thermal sensor may temporally lag behind actual respiration, as it takes time for the surface temperature detected by the thermal sensor to change in response to a change in respiration (breathing in or out), while up or down motion of the surface of the skin detected by a motion sensor corresponds in time with breathing in or out. Thus, the signals from the different types of sensors may need to be aligned before using them in combination to estimate respiration rate, changes in respiration, etc. As another example, signals from other sensors, such as head motion sensors, may be input to processors

752, and a lock-in amplification technique may be used to reject relative HMD motion from the motion sensor 710 signal to thus provide a cleaner signal of motion of the user's face detected by the motion sensor(s) 710.

In some embodiments, sensors 710 may include one or more contact-based audio accelerometers, also referred to as motion sensors, that are roughly 2×2 mm in size and that may contact the surface of a user's face. Motion data from the surface collected by these motion sensors and pre-processed by processors 752 may be analyzed by processors 754 and used to estimate respiration rate and/or to detect changes in respiration. In some embodiments, sensors 710 may instead or also include one or more thermal sensors implemented as single-pixel or small multi-pixel (e.g., 4×4) non-contact infrared detectors. Instead or in addition, sensors 710 may include thermal sensors implemented as thermistors and/or thermocouples. These thermal sensors 710 may collect thermal data from the surface of the user's face (or other regions of the user's head). Thermal data collected from the surface by the thermal sensors 710 may be analyzed and used to estimate respiration rate and/or detect changes in respiration, alone or in combination with motion data collected by one or more motion sensors 710. In some embodiments, thermal data collected by the thermal sensors 710 may instead or also be used to estimate core body temperature.

Processors 754 may be configured to analyze and process data collected by sensors 710 to generate biometric data including, but not limited to, respiration data including respiration rate and changes in respiration, and thermal data including but not limited core body temperature. This biometric data may, for example, be provided to the user visually (graphically and/or textually) via a display of the HMD 700. In some embodiments, biometric data may instead or also be presented in audio form, for example via an audio signal to the user via headphones or earbuds. In some embodiments, the biometric data may be stored to memory of the HMD 700. In some embodiments, biometric data may be transmitted via a wired or wireless connection to an external device, such as a smartphone, pad or tablet, or laptop computer, and video or audio representations of the biometric data may be presented to the user via the external device, or stored on the external device.

In some embodiments, other components 720 of an HMD 700 may be used in determining temperature and/or respiration. In some embodiments, for example, visible light and/or IR cameras that are used for other purposes may be leveraged to collect biometric data. As an example, signals from IR cameras used in gaze tracking and/or from visible light cameras used for capturing images of portions of the user's face may be subsampled in regions of interest, and the subsampled data may be pre-processed 752 and analyzed 754 to estimate surface temperature or changes in temperature. This data may, for example, be used in determining respiration or changes in respiration, alone or in combination with data collected from sensors 710.

In some embodiments, other biometric sensors (not shown), such as photo-plethysmography (PPG) sensors, may be integrated in an HMD 700; data collected from these other sensors may be used alone or in combination with the respiration and temperature data collected by the motion and thermal sensors 710 of the HMD 700, for example to report current biometric data to the user as feedback, recorded for use in tracking biometric data over time, and so on.

In some embodiments, biometric data, including one or more of, but not limited to, thermal data, pulse, and respiration data, may be collected by sensors on one or more devices 780 external to the HMD 700, for example from a wristband, headphones, or earbuds. Data collected from these sensors in device(s) 780 may be pre-processed 752 and analyzed 754, and may be used alone or in combination with the data collected by the sensors 710 of the HMD 700, for example to report current biometric data to the user as feedback, to be recorded for use in tracking biometric data over time, and so on.

Figure 8:
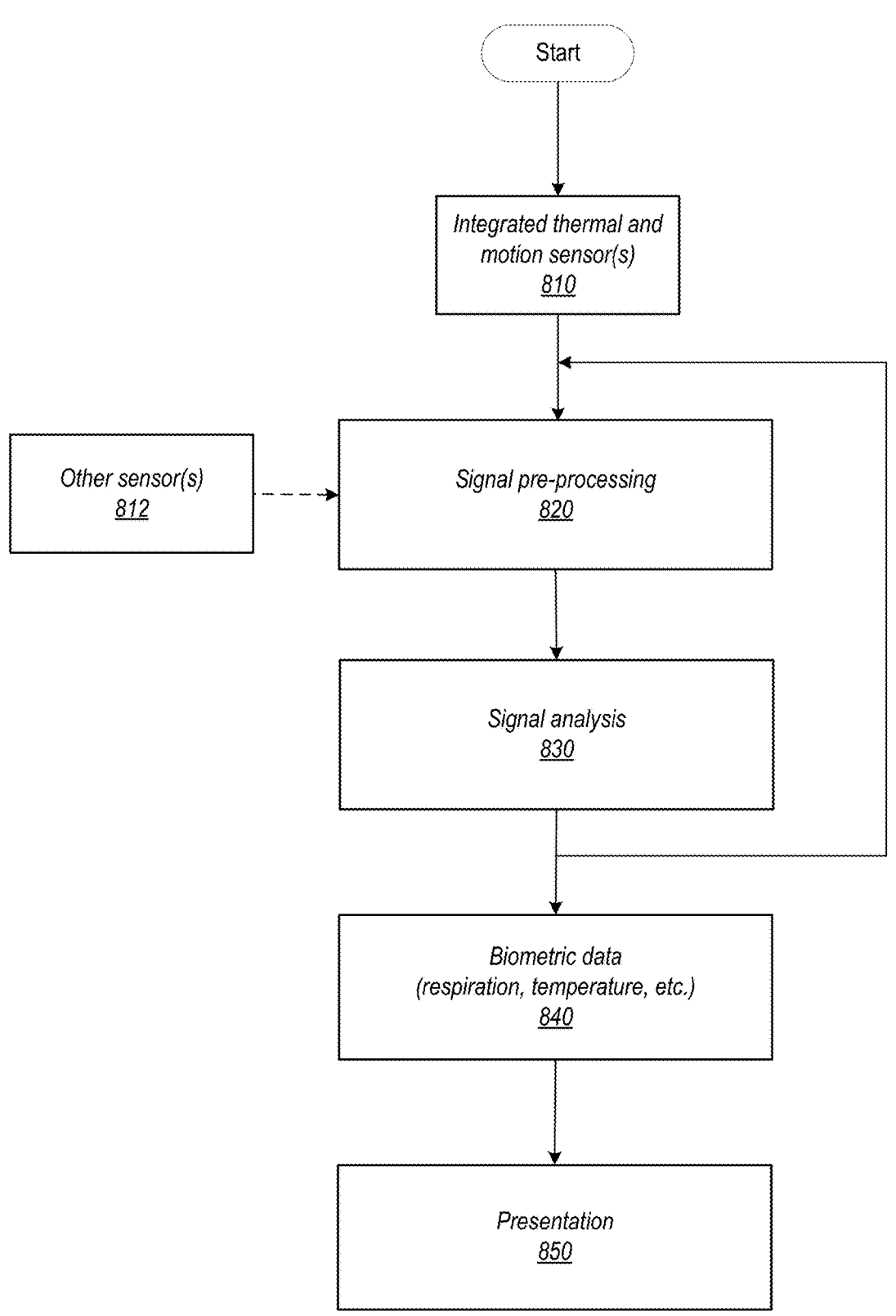
FIG. 8 is a block diagram illustrating collection and processing of biometric data in an HMD, according to some embodiments.

FIG. 8 is a block diagram illustrating collection and processing of biometric data in an HMD, according to some embodiments. Integrated thermal and/or motion sensors 810 may collect thermal and motion data for a user wearing the HMD as described in reference to FIGS. 1 through 7. The raw data collected by the sensors 810 may be pre-processed 820, for example to align signals from different sensors that are out of phase. As another example, signals from one or more other sensors 812, such as head motion sensors of the HMD, may be input to the signal pre-processing block 820, and a lock-in amplification technique may be used to reject relative HMD motion from the motion sensor 810 signal to thus provide a cleaner signal of the motion of the user's face detected by the motion sensor(s) 810.

The signals may then be analyzed 830 to generate biometric data 840 including but not limited to respiration and temperature data. The generated biometric data may then be presented 850 to the user, for example in visual and/or audio form. The biometric data may also be recorded for use in tracking biometric data over time, or transmitted to an external device via a wired or wireless connection.

In some embodiments, biometric data collected by other sensors 812, for example sensors in devices external to the HMD or other types of sensor components of the HMD, may also be pre-processed and analyzed to generate the biometric data.

As indicated by the arrow returning from element 830 to element 820, the collection and processing of the signals from sensors to generate biometric data may be a continuous process as long as the user is using the HMD (and has the biometric data functionality enabled).

Figure 9:
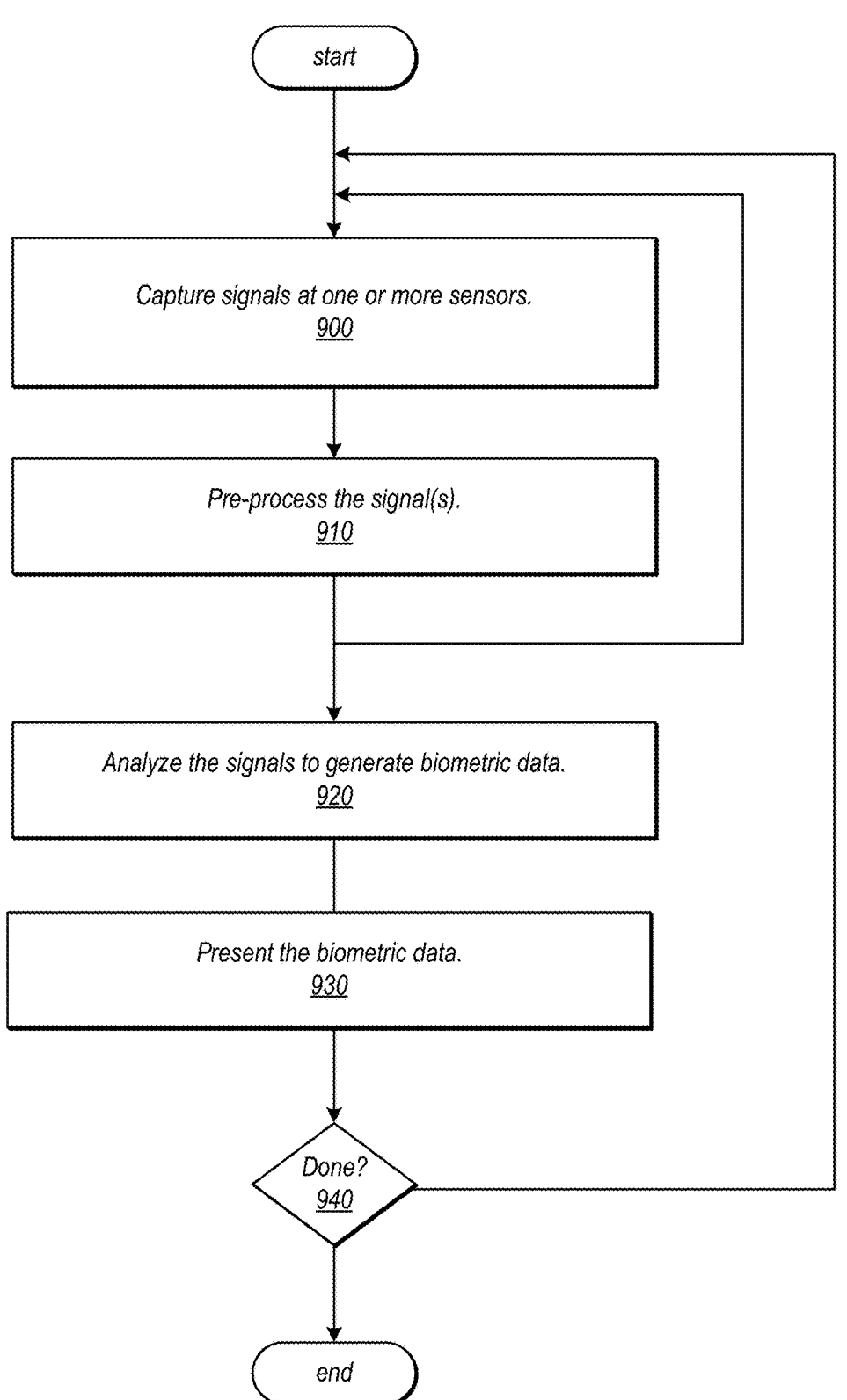
FIG. 9 is a flowchart of a method for collecting and processing biometric data in an HMD, according to some embodiments.

FIG. 9 is a flowchart of a method for collecting and processing biometric data in an HMD, according to some embodiments. As indicated at 900, thermal and motion data are captured by one or more integrated thermal and/or motion sensors. As indicated at 910, the raw data collected by the sensors may be pre-processed, for example to align signals from different sensors that are out of phase, or to filter out head motion detected by other sensors from the motion signal detected by the contact accelerometer sensors. As indicated at 920, the signals may then be analyzed to generate biometric data including but not limited to respiration and temperature data. As indicated at 930, the generated biometric data may then be presented to the user, for example in visual and/or audio form. The biometric data may also be recorded for use in tracking biometric data over time, or transmitted to an external device via a wired or wireless connection.

In some embodiments, biometric data collected by other 812, for example sensors in devices external to the HMD or other types of sensor components of the HMD, may also be pre-processed 910 and analyzed 920 to generate the biometric data As indicated by the arrow returning from element 940 to element 900, the collection and processing of the signals from sensors to generate biometric data may be a continuous process as long as the user is using the HMD and has the biometric data functionality enabled.

Respiration and Temperature Detection

The following sections further describe accelerometer based respiration detection, passive infrared (thermal) respiration detection, and body temperature measurement methods and apparatus using motion and thermal sensors integrated in or attached to an HMD as described in reference to FIGS. 1A through 9.

Respiration Detection

Respiration detection has been conventionally performed using a band worn by a subject and/or using a flow-meter in-line with the subject's mouth or nose (or both). These conventional methods are not designed for long-term user comfort, and are not easily integrated with an HMD. Further, respiration rate may be difficult to accurately estimate using conventional methods such as PPG sensors in a wristband.

Audio accelerometers have been used for contact-based extraction of speech through the physics of bone-conduction between the voice box and head. A widespread use of bone-conduction accelerometers are in wireless headphones. These audio accelerometers are extremely sensitive and support broadband frequencies up to 4 kHz.

Small, high-bandwidth audio accelerometers (also referred to as motion sensors) are described that are roughly 2×2 mm, surface mount, and that integrate with signal processing and processors of an HMD. These audio accelerometers are adapted for use in contact-based respiration estimation in an HMD as described herein. Providing the contact accelerometers to detect respiration in an HMD as described herein may provide a more direct measure of respiration than conventional methods. In addition, subtle changes in surface temperature of, for example, the surface of the nose may be detected using thermal sensors as described herein and used to determine respiration rate and changes. The data from motion sensors or thermal sensors may be used alone to detect respiration rate and change, or the data from motion sensors or thermal sensors may be used in combination to possibly provide an even more accurate estimate of respiration rate and change.

Conventional thermal detection methods have employed contact-based sensors such as thermistors and thermocouples, which can be challenging to integrate in small form factor devices, and which require low thermal mass designs with constant contact with the skin. Conventional non-contact methods for thermal detection have employed thermal imaging cameras with resolutions of 320×240; image processing techniques are used to extract facial features and to isolate regions of known large thermal delta (nose, mouth). However, this approach requires an outward view of the user, and the cameras tend to be expensive and relatively large.

Embodiments of an unobtrusive, non-contact method for respiration measurement using non-contact thermal sensors are described that may be integrated in HMDs. Embodiments are described that use one or more passive infrared sensors that include a one or more infrared-detecting "pixels"; the non-contact passive infrared sensors are arranged near the nose (or alternatively near some other part of the face) such that the minute temperature differences created by normal respiration are measured. Some embodiments may leverage a multi-sensor or multi-pixel array passive infrared (IR) sensor which can provide a wider field of view, and the system may be configured to adaptively sub-sample only the necessary pixels from the array that required for respiration measurement.

Respiration data derived from the signals from the passive infrared sensor(s) may be used alone or in combination with respiration data derived from the signals of contact accelerometers as described above.

Detecting respiration rate and changes in respiration may be used in many applications. Detecting respiration rate and changes may, for example, be used as a non-invasive method of tracking a user's psychological and emotional state, as well as their physiological state. For example, respiration data may indicate a fight-or-flight response (stress, anxiety). In such a response, blood rushes away from the entire outer layer of the body, not just the face, to fuel the muscles. Respiration may increase, and surface body temperature may decrease due to the drop in circulation at the surface. Contact-based accelerometers (motion sensors) as described herein, for example in contact with the surface of the user's nose, may be used to detect motion of the user's face, and this motion may be analyzed to derive respiration rate and detect changes in respiration.

Providing the contact accelerometers and/or contact or non-contact thermal sensors to detect respiration in an HMD as described herein may thus provide a more direct measure of respiration than conventional methods.

Surface temperature and changes thereof may also be detected and tracked using thermistors, thermocouples, and/or passive infrared thermal sensors as described herein. Differences in respiration rate detected by the motion sensors in combination with surface temperature of the user's skin may be used to distinguish between different affective states (e.g., stress vs embarrassment).

The respiration data generated by embodiments may be presented to the user using visual, audio, or other methods. This information may, for example, be used in an application to enhance relaxation via biofeedback. The respiration data may also be recorded. The recorded data may, for example, used to track biometric data over time. The biometric data collected on the HMD may also be transmitted to another device such as a smartphone, tablet or pad, or notebook computer via a wired or wireless connection, and displayed or stored on that device.

Security measures such as encryption and/or password protection may be implemented in software and/or hardware on the HMD to ensure that biometric data for a user collected on an HMD using the motion and thermal sensors as described herein is protected and kept private.

As illustrated in FIGS. 1A-1B and 4A-4B, contact and/or non-contact motion and thermal sensors as described herein may be integrated in a soft, flexible nose mount. The nose mount may be configured to ensure that contact sensors such as audio accelerometer(s) touch the surface of the nose comfortably. The nose mount may be configured to couple maximal vibration energy from the nose and mount as a result of respiration. In addition, the nose mount may be configured to ensure that non-contact sensors such as passive infrared sensors are at an optimal distance from and normal to the surface of the nose.

Instead or in addition, contact and/or non-contact motion and thermal sensors as described herein may be integrated in a light/face seal, for example in the cheek or brow region, as illustrated in FIGS. 2A-2B and 4A-4B.

Instead or in addition, contact and/or non-contact motion and thermal sensors as described herein may be integrated elsewhere in an HMD, for example as illustrated in FIGS. 3A-3B and 4A-4B.

Embodiments of an HMD may thus include one or more high-bandwidth accelerometers (motion sensors) with one or more acceleration axes that are in contact with the nasal region and positioned to extract respiration-induced vibrations. Embodiments may instead or also include one or more non-contact thermal sensors as described herein. Processors on the HMD (or on an external device) may be configured to process signals from the accelerometers and/or thermal sensors to estimate respiration rate and detect changes in respiration. The accelerometers may be integrated in a compliant nasal mount that is positioned to ensure contact of the audio accelerometer(s) with the surface of a user's nose. The non-contact thermal sensors may also be integrated in a compliant nasal mount configured to position the thermal sensors at an optimal distance from and normal to the surface of the nose. In some embodiments, the processors may be configured to perform signal processing to incorporate multiple high-bandwidth accelerometer signals and/or thermal sensor signals to increase respiration extraction resolution. Some embodiments may include a frequency estimation signal processing block based on lock-in amplification techniques that are additionally adapted to accept input from additional sensors of the HMD and/or from other sensors; the input from the additional sensors may be used to reject relative head mounted device motion relative to the user that may be present in the accelerometer signals.

In some embodiments, the system may be configured to leverage data from other wearable sensors (e.g. a PPG sensor on a watch or wristband) and/or other sensors of the HMD to increase respiration accuracy, contextual awareness, and to reduce time to first respiration rate output.

In some embodiments, the system may be configured to provide visual and/or audio feedback to the user wearing the HMD based on the respiration data collected by the accelerometers and/or thermal sensors and processed by the processors. For example, respiration sounds may be generated and fed to the user via earbuds or headphones based on the respiration data collected by the accelerometers integrated in the HMD. This may, for example provide the user with a more immersive experience in a virtual reality application implemented on the HMD.

Some embodiments of an HMD may thus include or more integrated passive infrared sensors integrated into a head mounted device to observe the nasal and mouth region surface-temperature time profiles and spatial gradients. Some embodiments may include a non-contact, compliant mount (e.g., nose mount) that includes one or more of the passive infrared sensors and configured to maintain distance and field of view across a variety of facial feature shapes and sizes. One or more of the passive infrared sensors may be connected to a processor and a signal processing chain capable of adaptively estimating respiration rate. In some embodiments, the processor and signal processing chain may leverage data from additional head mounted device sensors such as cameras and inertial measurement units to process signals from the thermal sensors. Some embodiments may include a frequency estimation signal processing block based on lock-in amplification techniques that is configured to accept input from additional sensors to reject relative head mounted device motion relative to the user. In some embodiments, the passive IR sensor system and signal processing chain may be configured to track long term nasal temperature and continual characterization as part of a suite of respiration and health quantifying sensors and signal processing chains integrated in the HMD and/or in external devices. In some embodiments, a passive infrared sensor system integrated in an HMD may leverage data from other wearable sensors (e.g. PPG sensors on a watch or wristband) to increase respiration accuracy and to reduce time to first respiration rate output.

In some embodiments, data from other sensors including but not limited to inertial sensors, inertial measurement units (IMUs) measuring head movement during breathing, cameras directed at other portions of the body such as the chest, data from microphone(s) that capture breathing sounds, and motion sensors that detect motion of the diaphragm, shoulders, or other body parts during breathing may be collected and analyzed along with the motion sensor and/or passive thermal sensor data to determine and track respiration rate.

Measuring Body Temperature

Instead of or in addition to using non-contact thermal sensors for measuring temperature of a region of a user's face such as the nose to estimate respiration rate, embodiments of thermal sensors integrated in an HMD for estimating body temperature (e.g., core body temperature) are described. Embodiments may allow body temperature of a user to be measured with integrated thermal sensors while wearing an HMD. The thermal sensors that may be used to measure body temperature in an HMD may include contact sensors, non-contact sensors, or both.

FIGS. 5A and 6A illustrate example contact sensors that may be used to measure body temperature. Contact sensors may, for example be mounted on or integrated in a nose pad, a light seal as shown in FIG. 2, in a nasal mount as shown in FIG. 1, or elsewhere in the HMD as shown in FIG. 3. Thermal contact sensors may include thermistor and/or thermocouple technology sensors. Thermistors measure temperature roughly linearly, and passively measure fluctuations in temperature. Thermistors are relatively inexpensive, and can easily be miniaturized. Contact thermal sensors may be used to measure temperature at the surface of the nose, or in other places such as the forehead, temple, or ear.

FIGS. 5B and 6B illustrate example non-contact sensors that may be used to measure body temperature. Non-contact sensors may, for example be mounted on or integrated in a nose pad, a light seal as shown in FIG. 2, a nasal mount as shown in FIG. 1, or elsewhere in the HMD as shown in FIG. 3. Thermal non-contact sensors may include, but are not limited to, passive IR sensors that include one or more pixels as illustrated in FIGS. 5B and 6B. Passive IR sensors may be used to measure temperature at the surface of the nose, or in other places such as the forehead, temple, or in the region around the eye.

In some embodiments, instead of or in addition to contact sensors and passive IR sensors as illustrated in FIGS. 5A through 6B, visible light (RGB) cameras of the HMD may be used to measure changes in luminance levels; this information may be analyzed to derive changes in body temperature. Similarly, in some embodiments, instead of or in addition to passive IR sensors, information captured with IR cameras of the HMD, for example IR cameras that are used in gaze tracking, may be subsampled and analyzed to derive changes in body temperature. In some embodiments, waveguides in lenses in front of the user's eyes may be leveraged to collect thermal data, which can be transmitted to a dedicated discrete sensor elsewhere in the HMD, for example at or near the temple in the HMD frame.

Information collected from the thermal sensors in an HMD may be used in a variety of applications. For example, a rise in temperature could be reported to the user as an indication that the user may be getting ill, or to alert the user that their core temperature is too high. As another example, fluctuations in temperature may be used to derive changes in respiration, as previously described. The respiration information may be used to detect possible anxiety or stress, and the user may be notified of this possibility. As another example, changes in temperature and/or respiration may be used to provide biofeedback to the user; this biofeedback may, for example, help the user to regulate their emotional state. As another example, this biofeedback may be used in a meditation application to help the user regulate their breathing, or in breath training applications in general. As another example, spatial audio (sounds played to the user via headphones, ear buds, or speakers) may be modulated based on the temperature/respiration data to help the user to relax. As another example, thermal data and/or respiration data derived at least in part from the thermal sensors may be used to detect whether the user is breathing through the mouth or through the nose, and this information may be provided as feedback to the user.

In some embodiments, information derived from the thermal sensors integrated in an HMD may also be used in combination with sensors in other devices, such as watches or wristbands. As an example, a watch or wrist band may include contact thermal sensors that measure temperature, as well as other sensors that collect biometric data. Thermal data directly measured by passive IR sensors in an HMD may be used to calibrate contact thermal sensors in a watch or wrist band. Alternatively, thermal data measured by thermal sensors in a watch or wrist band may be used to calibrate the passive IR sensors in an HMD.

Body temperature data collected by the thermal sensors of an HMD, and/or respiration data derived from the thermal data, may be recorded or stored to memory of the HMD or on a device external to the HMD. The recorded data may, for example, be used to track biometric data for the user over time. Security measures such as encryption and/or password protection may be implemented in software and/or hardware on the HMD to ensure that biometric data for a user collected on an HMD using the motion and thermal sensors as described herein is protected and kept private.

Example Systems

Embodiments of methods and apparatus for measuring biometric data including respiration and temperature as described herein may, for example, be used in head-mounted devices (HMD), for example HMDs of computer-generated reality (XR) systems such as a mixed or augmented reality (MR) systems or virtual reality (VR) systems.

A device that implements methods and apparatus for measuring biometric data including respiration and temperature as illustrated in FIGS. 1A through 9 may include a controller comprising one or more processors and memory. Controller may include one or more of various types of processors, image signal processors (ISPs), graphics processing units (GPUs), coder/decoders (codecs), and/or other components for processing and rendering video and/or images. In some embodiments, the controller may be integrated in the device. In some embodiments, at least some of the functionality of the controller may be implemented by an external device coupled to the device by a wired or wireless connection. In some embodiments, the controller may be coupled to an external memory for storing and reading data and/or software.

Figure 10:
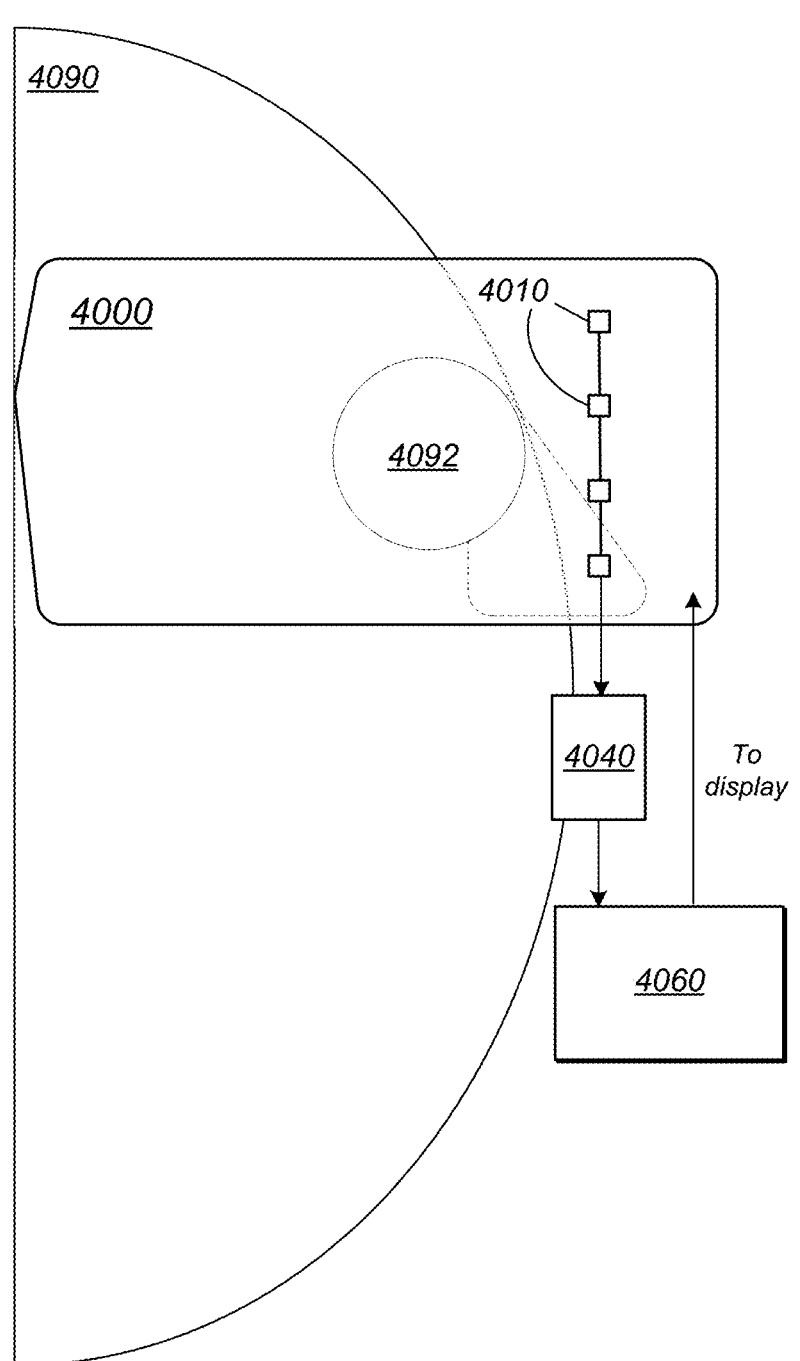
FIG. 10 illustrates an example head-mounted device (HMD) that may include components and implement methods as illustrated in FIGS. 1 through 9, according to some embodiments.

FIG. 10 illustrates an example head-mounted device (HMD) that may include components and implement methods as illustrated in FIGS. 1 through 9, according to some embodiments. An HMD 4000 may, for example be a component in a mixed or augmented reality (MR) system. Note that HMD 4000 as illustrated in FIG. 10 is given by way of example, and is not intended to be limiting. In various embodiments, the shape, size, and other features of an HMD 4000 may differ, and the locations, numbers, types, and other features of the components of an HMD 4000 may vary. In some embodiments, HMD 4000 may include, but is not limited to, a display and two optical lenses (eyepieces) (not shown), mounted in a wearable housing or frame. Alternatively, HMD 4000 may include a display but not eyepieces. As shown in FIG. 10, HMD 4000 may be positioned on the user's head 4090 such that the display is disposed in front of the user's eyes 4092. The HMD 4000 may also include one or more thermal and/or motion sensors 4010 as described herein in reference to FIGS. 1A through 9.

While not shown, HMD 4000 may also include other sensors that collect information about the user's environment (video, depth information, lighting information, etc.) and about the user (e.g., eye tracking sensors). The other sensors may include one or more of, but are not limited to one or more eye cameras (e.g., infrared (IR) cameras) that capture views of the user's eyes 4092, one or more scene (visible light) cameras (e.g., RGB video cameras) that capture images of the real world environment in a field of view in front of the user (not shown), and one or more ambient light sensors that capture lighting information for the environment (not shown).

Figure 11:
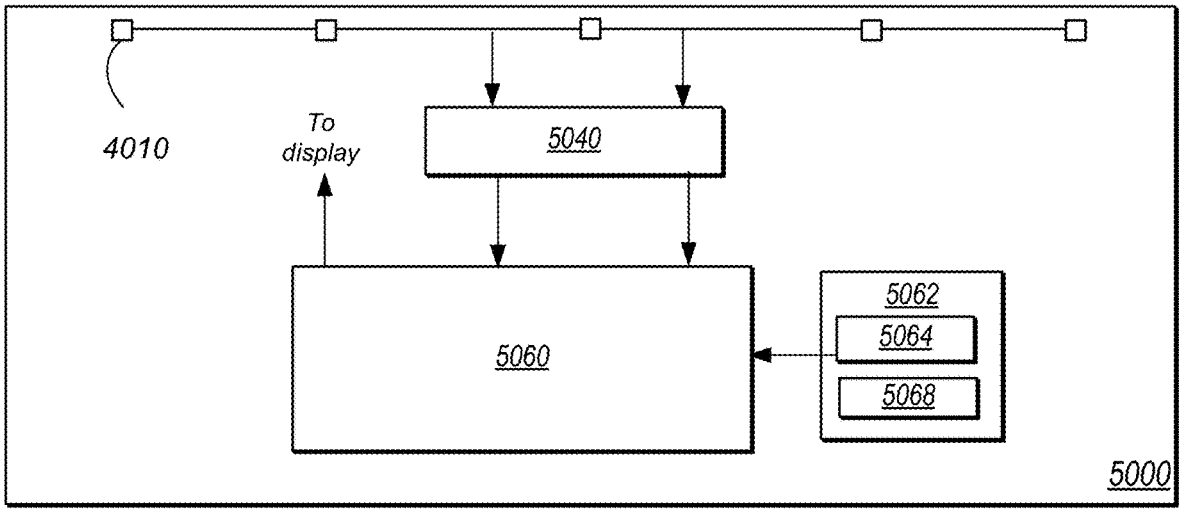
FIG. 11 is a block diagram illustrating an example system that may include components and implement methods as illustrated in FIGS. 1 through 9, according to some embodiments.

A controller 4060 for the MR system may be implemented in the HMD 4000, or alternatively may be implemented at least in part by an external device (e.g., a computing system) that is communicatively coupled to HMD 4000 via a wired or wireless interface. Controller 4060 may include one or more of various types of processors, image signal processors (ISPs), graphics processing units (GPUs), coder/decoders (codecs), and/or other components for processing and rendering video and/or images. Controller 4060 may render frames (each frame including a left and right image) that include virtual content based at least in part on inputs obtained from the sensors, and may provide the frames to the display. FIG. 11 further illustrates components of an HMD and MR system, according to some embodiments.

The HMD 4000 may include one or more processors 4040 configured to pre-process signals from the sensors 4010 as described herein; controller 4060 may be configured to analyze the pre-processed signals to estimate, generate, and output biometric information including but not limited to temperature and respiration information. The biometric information may be output to the display. Instead or in addition, biometric information may be provided in audible form to the user, for example via earbuds or headphones coupled to or integrated in the HMD 4000. In some embodiments, biometric information may be recorded, for example to memory of the HMD; the recorded biometric data may, for example, be used to track changes in respiration over time. In some embodiments, biometric information may be transmitted to another device via a wired or wireless connection.

Embodiments of an HMD 4000 as illustrated in FIG. 10 may, for example, be used in augmented or mixed (AR) applications to provide augmented or mixed reality views to the user 4090. HMD 4000 may include one or more sensors, for example located on external surfaces of the HMD 4000, which collect information about the user 4090's external environment (video, depth information, lighting information, etc.); the sensors may provide the collected information to controller 4060 of the MR system. The sensors may include one or more visible light cameras (e.g., RGB video cameras) that capture video of the user's environment that may be used to provide the user 4090 with a virtual view of their real environment. In some embodiments, video streams of the real environment captured by the visible light cameras may be processed by the controller 4060 of the HMD 4000 to render augmented or mixed reality frames that include virtual content overlaid on the view of the real environment, and the rendered frames may be provided to the HMD 4000's display system.

FIG. 11 is a block diagram illustrating an example MR system that may include components and implement methods as illustrated in FIGS. 1 through 9, according to some embodiments. In some embodiments, a MR system may include an HMD 5000 such as a headset, helmet, goggles, or glasses. HMD 5000 may implement any of various types of display technologies. For example, the HMD 5000 may include a display system that displays frames including left and right images on screens or displays (not shown) that are viewed by a user through eyepieces (not shown). The display system may, for example, be a DLP (digital light processing), LCD (liquid crystal display), or LCOS (liquid crystal on silicon) technology display system. To create a three-dimensional (3D) effect in a 3D virtual view, objects at different depths or distances in the two images may be shifted left or right as a function of the triangulation of distance, with nearer objects shifted more than more distant objects. Note that other types of display systems may be used in some embodiments.

In some embodiments, HMD 5000 may include a controller 5060 configured to implement functionality of the MR system and to generate frames (each frame including a left and right image) that are provided to the HMD's displays. In some embodiments, HMD 5000 may also include a memory 5062 configured to store software (code 5064) of the MR system that is executable by the controller 5060, as well as data 5068 that may be used by the MR system when executing on the controller 5060. In some embodiments, HMD 5000 may also include one or more interfaces (e.g., a Bluetooth technology interface, USB interface, etc.) configured to communicate with an external device via a wired or wireless connection. In some embodiments, at least a part of the functionality described for the controller 5060 may be implemented by an external device. The external device may be or may include any type of computing system or computing device, such as a desktop computer, notebook or laptop computer, pad or tablet device, smartphone, hand-held computing device, game controller, game system, and so on.

In various embodiments, controller 5060 may be a uniprocessor system including one processor, or a multiprocessor system including several processors (e.g., two, four, eight, or another suitable number). Controller 5060 may include central processing units (CPUs) configured to implement any suitable instruction set architecture, and may be configured to execute instructions defined in that instruction set architecture. For example, in various embodiments controller 5060 may include general-purpose or embedded processors implementing any of a variety of instruction set architectures (ISAs), such as the x86, PowerPC, SPARC, RISC, or MIPS ISAs, or any other suitable ISA. In multiprocessor systems, each of the processors may commonly, but not necessarily, implement the same ISA. In some embodiments, controller 5060 may be implemented as a system on a chip (SoC). For example, in some embodiments, processors, memory, I/O interface (e.g. a fabric), etc. may be implemented in a single SoC comprising multiple components integrated into a single chip. For example an SoC may include multiple CPU cores, a multi-core GPU, a multi-core neural engine, cache, one or more memories, etc. integrated into a single chip. In some embodiments, an SoC embodiment may implement a reduced instruction set computing (RISC) architecture, or any other suitable architecture. Controller 5060 may employ any microarchitecture, including scalar, superscalar, pipelined, superpipelined, out of order, in order, speculative, non-speculative, etc., or combinations thereof. Controller 5060 may include circuitry to implement microcoding techniques. Controller 5060 may include one or more processing cores each configured to execute instructions. Controller 5060 may include one or more levels of caches, which may employ any size and any configuration (set associative, direct mapped, etc.). In some embodiments, controller 5060 may include at least one graphics processing unit (GPU), which may include any suitable graphics processing circuitry. Generally, a GPU may be configured to render objects to be displayed into a frame buffer (e.g., one that includes pixel data for an entire frame). A GPU may include one or more graphics processors that may execute graphics software to perform a part or all of the graphics operation, or hardware acceleration of certain graphics operations. In some embodiments, controller 5060 may include one or more other components for processing and rendering video and/or images, for example image signal processors (ISPs), coder/decoders (codecs), etc.

Memory 5062 may include any type of memory, such as dynamic random access memory (DRAM), synchronous DRAM (SDRAM), double data rate (DDR, DDR2, DDR3, etc.) SDRAM (including mobile versions of the SDRAMs such as mDDR3, etc., or low power versions of the SDRAMs such as LPDDR2, etc.), RAMBUS DRAM (RDRAM), static RAM (SRAM), etc. In some embodiments, one or more memory devices may be coupled onto a circuit board to form memory modules such as single inline memory modules (SIMMs), dual inline memory modules (DIMMs), etc. Alternatively, the devices may be mounted with an integrated circuit implementing system in a chip-on-chip configuration, a package-on-package configuration, or a multi-chip module configuration.

In some embodiments, the HMD 5000 may include one or more sensors that collect information about the user's environment (video, depth information, lighting information, etc.). The sensors may provide the information to the controller 5060 of the MR system. In some embodiments, the sensors may include, but are not limited to, visible light cameras (e.g., video cameras) and ambient light sensors.

The HMD 5000 may also include one or more thermal and/or motion sensors 5010 as described herein in reference to FIGS. 1A through 9. The HMD 5000 may include one or more processors 5040 configured to pre-process signals from the sensors 5010 as described herein; controller 5060 may be configured to analyze the pre-processed signals to estimate, generate, and output biometric information including but not limited to temperature and respiration information. The biometric information may be output to the display. Instead or in addition, biometric information may be provided in audible form to the user, for example via earbuds or headphones coupled to or integrated in the HMD 5000. In some embodiments, biometric information may be recorded, for example to memory 5062; the recorded biometric data may, for example, be used to track changes in respiration over time. In some embodiments, biometric information may be transmitted to another device via a wired or wireless connection.

In some embodiments, the HMD 5000 may be configured to render and display frames to provide an augmented or mixed reality (MR) view for the user based at least in part according to sensor inputs. The MR view may include renderings of the user's environment, including renderings of real objects in the user's environment, based on video captured by one or more video cameras that capture high-quality, high-resolution video of the user's environment for display. The MR view may also include virtual content (e.g., virtual objects, virtual tags for real objects, avatars of the user, etc.) generated by MR system and composited with the displayed view of the user's real environment.

Embodiments of the HMD 5000 as illustrated in FIG. 11 may also be used in virtual reality (VR) applications to provide VR views to the user. In these embodiments, the controller 5060 of the HMD 5000 may render or obtain virtual reality (VR) frames that include virtual content, and the rendered frames may be displayed to provide a virtual reality (as opposed to mixed reality) experience to the user. In these systems, rendering of the VR frames may be affected based on the point of gaze determined from the imaging system.

Extended Reality

A real environment refers to an environment that a person can perceive (e.g. see, hear, feel) without use of a device. For example, an office environment may include furniture such as desks, chairs, and filing cabinets; structural items such as doors, windows, and walls; and objects such as electronic devices, books, and writing instruments. A person in a real environment can perceive the various aspects of the environment, and may be able to interact with objects in the environment.

An extended reality (XR) environment, on the other hand, is partially or entirely simulated using an electronic device. In an XR environment, for example, a user may see or hear computer generated content that partially or wholly replaces the user's perception of the real environment. Additionally, a user can interact with an XR environment. For example, the user's movements can be tracked and virtual objects in the XR environment can change in response to the user's movements. As a further example, a device presenting an XR environment to a user may determine that a user is moving their hand toward the virtual position of a virtual object, and may move the virtual object in response. Additionally, a user's head position and/or eye gaze can be tracked and virtual objects can move to stay in the user's line of sight.

Examples of XR include augmented reality (AR), virtual reality (VR) and mixed reality (MR). XR can be considered along a spectrum of realities, where VR, on one end, completely immerses the user, replacing the real environment with virtual content, and on the other end, the user experiences the real environment unaided by a device. In between are AR and MR, which mix virtual content with the real environment.

VR generally refers to a type of XR that completely immerses a user and replaces the user's real environment. For example, VR can be presented to a user using a head mounted device (HMD), which can include a near-eye display to present a virtual visual environment to the user and headphones to present a virtual audible environment. In a VR environment, the movement of the user can be tracked and cause the user's view of the environment to change. For example, a user wearing a HMD can walk in the real environment and the user will appear to be walking through the virtual environment they are experiencing. Additionally, the user may be represented by an avatar in the virtual environment, and the user's movements can be tracked by the HMD using various sensors to animate the user's avatar.

AR and MR refer to a type of XR that includes some mixture of the real environment and virtual content. For example, a user may hold a tablet that includes a camera that captures images of the user's real environment. The tablet may have a display that displays the images of the real environment mixed with images of virtual objects. AR or MR can also be presented to a user through an HMD. An HMD can have an opaque display, or can use a see-through display, which allows the user to see the real environment through the display, while displaying virtual content overlaid on the real environment.

There are many types of devices that allow a user to experience the various forms of XR. Examples include HMDs, heads up displays (HUDs), projector-based systems, smart windows, tablets, desktop or laptop computers, smart watches, earbuds/headphones, controllers that may include haptic devices, and many others. As mentioned above, an HMD, or any of the other devices listed above may include opaque displays (e.g. liquid crystal displays (LCDs), organic light emitting diode (OLED) displays or micro-LED displays) or see through displays. A see through display can have a medium through which light is directed to a user's eyes. The medium can include one or more of a waveguide, hologram medium, optical combiner, optical reflector and other optical components. An image can be generated and propagated through the medium using a display source such as OLEDs, micro-LEDs, liquid crystal on silicon (LCOS), a light scanner, digital light projection (DLP).

Devices for XR may also include audio output devices such as speakers to present audio (including spatial audio) to users, haptics devices to stimulate the user's sense of touch, and other devices to stimulate any of the user's senses. Additionally, the device may include numerous sensors, including cameras, microphones, depth sensors, eye tracking sensors, environmental sensors, input sensors, and other sensors to allow the device to understand the user and the real environment.

Various embodiments as described herein are reflected in the following clauses:

Clause 1. A system, comprising:
a frame configured to be worn on a head;
one or more thermal sensors integrated in or coupled to the frame and configured to collect thermal data from a surface of the head; and
a controller comprising one or more processors configured to:
process the thermal data collected by the one or more thermal sensors to generate biometric data; and
present the biometric data.

Clause 2. The system as recited in clause 1, wherein, to process the thermal data collected by the one or more thermal sensors to generate biometric data, the controller is configured to process the thermal data collected by the one or more thermal sensors to estimate core body temperature.

Clause 3. The system as recited in clause 1, wherein, to process the thermal data collected by the one or more thermal sensors to generate biometric data the controller is configured to process the thermal data collected by the one or more thermal sensors to estimate respiration rate.

Clause 4. The system as recited in clause 1, wherein the thermal sensors include contact thermal sensors configured to contact the surface of a face.

Clause 5. The system as recited in clause 4, wherein the contact thermal sensors are thermistors or thermocouples.

Clause 6. The system as recited in clause 1, wherein the thermal sensors include non-contact thermal sensors that do not contact the surface of a face.

Clause 7. The system as recited in clause 6, wherein the non-contact thermal sensors include passive infrared sensors configured to detect infrared radiation from a portion of the surface of the face.

Clause 8. The system as recited in clause 6, wherein the non-contact thermal sensors are integrated in diaphragms configured to align a surface of the non-contact thermal sensors approximately normal to the surface of the face.

Clause 9. The system as recited in clause 1, further comprising a flexible nose mount coupled to or integrated in the frame, wherein at least one of the thermal sensors is integrated in the nose mount and configured to detect temperature of the surface of the nose.

Clause 10. The system as recited in clause 1, wherein the frame further comprises a light seal configured to conform to the face, wherein at least one of the thermal sensors is integrated in the light seal and configured to detect temperature of the surface of the face.

Clause 11. The system as recited in clause 1, wherein the thermal sensors include one or more cameras coupled to the frame, wherein the controller is further configured to subsample and process data captured by the one or more cameras to estimate temperature at portions of the surface of the face captured by the one or more cameras.

Clause 12. The system as recited in clause 11, wherein the one or more cameras include infrared cameras configured to capture views of the eye region for use in gaze tracking.

Clause 13. The system as recited in clause 11, wherein the one or more cameras include visible light cameras configured to capture views of portions of the face.

Clause 14. The system as recited in clause 1, wherein, to process the thermal data collected by the one or more thermal sensors to generate biometric data, the controller is configured to:
pre-process one or more signals from the one or more thermal sensors; and
analyze the pre-processed one or more signals to generate the biometric data.

Clause 15. The system as recited in clause 1, further comprising a display coupled to the frame, wherein, to present the biometric data, the controller is configured to present the biometric data in graphical or textual format.

Clause 16. The system as recited in clause 1, wherein the system is a head-mounted device (HMD).

Clause 17. A method, comprising:
performing, by a controller comprising one or more processors:
receiving thermal data for a surface of a face from or more thermal sensors integrated in or coupled to a head-mounted device (HMD);
processing the thermal data received from the one or more thermal sensors to generate biometric data; and
presenting the biometric data.

Clause 18. The method as recited in clause 17, wherein processing the thermal data received from the one or more thermal sensors to generate biometric data comprises processing the thermal data collected by the one or more thermal sensors to estimate core body temperature.

Clause 19. The method as recited in clause 17, wherein processing the thermal data received from the one or more thermal sensors to generate biometric data comprises processing the thermal data collected by the one or more thermal sensors to estimate respiration rate.

Clause 20. The method as recited in clause 17, wherein the thermal sensors include non-contact passive infrared sensors configured to detect infrared radiation from a portion of the surface of the face.

Clause 21. The method as recited in clause 17, wherein the thermal sensors are integrated in a flexible nose mount coupled to or integrated in the HMD.

Clause 22. The method as recited in clause 17, wherein the thermal sensors are integrated in a light seal of the HMD.

Clause 23. The method as recited in clause 17, wherein the thermal sensors include one or more cameras coupled to the frame, the method further comprising subsampling and processing data captured by the one or more cameras to estimate temperature at portions of the surface of the face captured by the one or more cameras.

Clause 24. The method as recited in clause 23, wherein the temperature estimated at one or more of the portions of the surface of the face is used in determining respiration or changes in respiration alone or in combination with the thermal data collected from the thermal sensors.

Clause 25. The method as recited in clause 23, wherein the one or more cameras include infrared cameras configured to capture views of the face's eye region for use in gaze tracking.

Clause 26. The method as recited in clause 23, wherein the one or more cameras include visible light cameras configured to capture views of portions of the face.

Clause 27. The method as recited in clause 17, wherein processing the thermal data received from the one or more thermal sensors to generate biometric data comprises:

pre-processing one or more signals from the one or more thermal sensors; and analyzing the pre-processed one or more signals to generate the biometric data.

Clause 28. The method as recited in clause 17, wherein presenting the biometric data comprises providing the biometric data to a display of the HMD in graphical or textual format.

Clause 29. The method as recited in clause 17, further comprising calibrating at least one thermal sensor in a device external to the HMD based on the thermal data received from the one or more thermal sensors of the HMD.

Clause 30. The method as recited in clause 29, wherein the device external to the HMD is a wrist band or watch.

The present technology may gather and use data from various sources to generate biometric data. This data, in some instances, may include personal information data that uniquely identifies a specific individual. This personal information data may include location-based data, demographic data, data or records associated with a user's health or fitness level (e.g., information associated with vital signs, medication, exercise, and the like), date of birth, or other personal or identifying information.

It is recognized that, in some instances, such personal information data may be used to benefit users. For example, the personal information data may be used to improve device security or health monitoring.

It is contemplated that the collection, disclosure, transfer, analysis, storage, or other use of personal information data should comply with well-established privacy policies or practices. Privacy policies and practices that are generally recognized as meeting or exceeding industry or governmental requirements for maintaining personal information data private and secure should be implemented and consistently used. These policies should be easily accessible and updated as the collection or use of the personal information data changes. Personal information data should be collected for legitimate and reasonable uses and not shared or sold outside of those legitimate uses. The collection or sharing should occur after receipt of the user's informed consent. Additional steps to safeguard and secure access to personal information data and to ensure that others with access to the personal information data adhere to their privacy policies and procedures should be considered. An evaluation by third parties to certify adherence to well-established privacy policies and practices may be performed. Policies and practices should be tailored to the particular types of personal information data being collected or accessed and adapted to applicable laws and standards, including jurisdiction-specific considerations. For example, the collection of or access to certain health data in the US may be governed by federal or state laws, such as the Health Insurance Portability and Accountability Act (HIPAA); whereas the collection of or access to the same health data may be subject to other regulations and policies in other countries. As such, different privacy practices should be implemented for different types of personal information data in each country.

It is contemplated that, in some instances, users may selectively prevent the use of, or access to, personal information data. Hardware or software features may be provided to prevent or block access to personal information data. For example, the present technology may be configured to allow users to "opt in" or "opt out" of the collection of personal information data during setup or anytime thereafter. In another example, users can select not to provide personal data with which biometric data could be associated. In yet another example, users can select to limit use of such personal data and/or biometric data. The present technology may also provide notifications relating to the access or use of personal information data. For example, a first notification may be provided in response to a user downloading an app that may access the user's personal information data and a second notification may be provided to remind the user just before the app accesses the personal information data.

Personal information data should be managed and handled to reduce the risk of unintentional or unauthorized access or use. Risk can be reduced by limiting the collection of data and deleting the data once it is no longer needed. When applicable, data de-identification may be used to protect a user's privacy. For example, de-identification may be performed by removing specific identifiers, controlling the specificity or amount of data stored (e.g., collecting home location data at a city level instead of at an address level), controlling how data is stored (e.g., aggregate data across multiple users), or other techniques.

Although the present technology may broadly include the use of personal information data, it may be implemented without accessing such personal information data. In other words, the present technology may not be rendered inoperable due to the lack of some or all of such personal information data. For example, only non-personal information data, a reduced amount of personal information data, or publicly available information, may be made available such that any biometric data is not accessible by others in a way that could be associated with a specific user.

The methods described herein may be implemented in software, hardware, or a combination thereof, in different embodiments. In addition, the order of the blocks of the methods may be changed, and various elements may be added, reordered, combined, omitted, modified, etc. Various modifications and changes may be made as would be obvious to a person skilled in the art having the benefit of this disclosure. The various embodiments described herein are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

What is claimed is:

1. A system, comprising:
a frame configured to be worn on a head;
one or more thermal sensors integrated in or coupled to the frame and configured to collect thermal data from a surface of the head, wherein the one or more thermal sensors include one or more passive non-contact infrared sensors integrated in one or more diaphragms configured to align a surface of the non-contact thermal sensors approximately normal to a surface of the head to detect infrared radiation from the surface of the head;
one or more infrared cameras coupled to the frame and configured to capture views of an eye region of the head for use in gaze tracking; and
a controller comprising one or more processors configured to:
    process the thermal data collected by the one or more thermal sensors, including data captured by the one or more passive non-contact infrared sensors, to generate biometric data separate from the gaze tracking; and
    present the biometric data.

2. The system as recited in claim 1, wherein, to process the thermal data collected by the one or more thermal sensors to generate biometric data, the controller is configured to process the thermal data collected by the one or more thermal sensors to estimate core body temperature.

3. The system as recited in claim 1, wherein, to process the thermal data collected by the one or more thermal sensors to generate biometric data, the controller is configured to process the thermal data collected by the one or more thermal sensors to estimate respiration rate.

4. The system as recited in claim 1, wherein the one or more thermal sensors further include contact thermal sensors configured to contact a surface of a face.

5. The system as recited in claim 1, wherein the one or more thermal sensors further include the one or more infrared cameras, wherein the thermal data collected by the one or more thermal sensors further includes data captured by the one or more infrared cameras to generate the biometric data separate from the gaze tracking.

6. The system as recited in claim 1, further comprising a flexible nose mount coupled to or integrated in the frame, wherein at least one of the thermal sensors is integrated in the nose mount and configured to detect temperature of a surface of a nose.

7. The system as recited in claim 1, wherein the frame further comprises a light seal configured to conform to a face, wherein at least one of the thermal sensors is integrated in the light seal and configured to detect temperature of a surface of the face.

8. The system as recited in claim 1, wherein the controller is further configured to subsample and process data captured by the one or more infrared cameras to estimate temperature at portions of a surface of a face captured by the one or more infrared cameras.

9. The system as recited in claim 1, wherein the one or more thermal sensors further include visible light cameras configured to capture views of portions of the face.

10. The system as recited in claim 1, wherein, to process the thermal data collected by the one or more thermal sensors to generate biometric data, the controller is configured to:
pre-process one or more signals from the one or more thermal sensors; and
analyze the pre-processed one or more signals to generate the biometric data.

11. The system as recited in claim 1, wherein the system is a head-mounted device (HMD).

12. A method, comprising:
performing, by a controller comprising one or more processors:
    receiving thermal data for a surface of a face from one or more thermal sensors integrated in or coupled to a head-mounted device (HMD), wherein the one or more thermal sensors include one or more passive non-contact infrared sensors integrated in one or more diaphragms configured to align a surface of the non-contact thermal sensors approximately normal to a surface of the head to detect infrared radiation from the surface of the head;
    processing the thermal data received from the one or more thermal sensors, including data captured by the one or more passive non-contact infrared sensors, to generate biometric data; and
    presenting the biometric data.

13. The method as recited in claim 12, wherein processing the thermal data received from the one or more thermal sensors to generate biometric data comprises processing the thermal data collected by the one or more thermal sensors to estimate core body temperature.

14. The method as recited in claim 12, wherein processing the thermal data received from the one or more thermal sensors to generate biometric data comprises processing the thermal data collected by the one or more thermal sensors to estimate respiration rate.

15. The method as recited in claim 12, wherein the thermal sensors include one or more cameras coupled to a frame, the method further comprising subsampling and processing data captured by the one or more cameras to estimate temperature at portions of a surface of the face captured by the one or more cameras.

16. The method as recited in claim 15, wherein the temperature estimated at one or more of the portions of the surface of the face is used in determining respiration or changes in respiration alone or in combination with the thermal data collected from the thermal sensors.

17. The method as recited in claim 15, wherein the one or more cameras include infrared cameras configured to capture views of a face's eye region for use in gaze tracking.

18. The method as recited in claim 12, wherein processing the thermal data received from the one or more thermal sensors to generate biometric data comprises:
pre-processing one or more signals from the one or more thermal sensors; and
analyzing the pre-processed one or more signals to generate the biometric data.

19. The method as recited in claim 12, further comprising calibrating at least one thermal sensor in a device external to the HMD based on the thermal data received from the one or more thermal sensors of the HMD.

* * * * *